United States Patent
Shuler

(10) Patent No.: US 12,168,090 B2
(45) Date of Patent: *Dec. 17, 2024

(54) BARRIER TO PREVENT OR REDUCE INGROWTH OF TISSUE

(71) Applicant: J&M Shuler Medical Inc., Athens, GA (US)

(72) Inventor: Michael Simms Shuler, Athens, GA (US)

(73) Assignee: J&M Shuler Medical Inc., Athens, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/234,103

(22) Filed: Aug. 15, 2023

(65) Prior Publication Data

US 2024/0033413 A1 Feb. 1, 2024

Related U.S. Application Data

(63) Continuation of application No. 17/515,896, filed on Nov. 1, 2021, now Pat. No. 11,766,514, which is a
(Continued)

(51) Int. Cl.
*A61M 1/00* (2006.01)
*A61F 13/0206* (2024.01)
*A61F 13/05* (2024.01)

(52) U.S. Cl.
CPC ............ *A61M 1/85* (2021.05); *A61F 13/0206* (2013.01); *A61F 13/05* (2024.01); *A61M 1/90* (2021.05);
(Continued)

(58) Field of Classification Search
CPC ............ A61F 13/05; A61M 1/90; A61M 1/85
See application file for complete search history.

(56) References Cited

U.S. PATENT DOCUMENTS

| 1,000,001 A | 8/1911 | Holz |
| 1,355,846 A | 10/1920 | Rannells |

(Continued)

FOREIGN PATENT DOCUMENTS

| AU | 2014291873 | 2/2016 |
| AU | 2013290346 | 6/2018 |

(Continued)

OTHER PUBLICATIONS

'o-wm.com' [online]. "Negative pressure wound therapy: "a rose by any other name"," Mar. 2005, [retrieved on Nov. 19, 2015]. Retrieved from the Internet: URLhttp://www.o-wm.com/content/negative-pressure-wound-therapy-%E2%80%9Ca-rose-any-other-name%E2%80%9D, 10 pages.
(Continued)

*Primary Examiner* — Sarah Al Hashimi
*Assistant Examiner* — Arjuna P Chatrathi
(74) *Attorney, Agent, or Firm* — Fish & Richardson P.C.

(57) ABSTRACT

A barrier for use in negative pressure wound therapy can include a base layer and surface structures. The barrier can be used to reduce or prevent tissue ingrowth. A method of using a negative pressure wound therapy system can include positioning a perforated barrier in a wound. After positioning the perforated barrier in the wound, positioning a pad in the wound on top of the perforated barrier, positioning a seal on top of the wound to at least partially seal the perforated barrier and the foam in the wound, and applying negative pressure wound therapy to the wound.

19 Claims, 16 Drawing Sheets

Related U.S. Application Data continuation of application No. 16/749,511, filed on Jan. 22, 2020, now Pat. No. 11,160,917.

(52) U.S. Cl.
CPC . *A61M 2205/32* (2013.01); *A61M 2205/3334* (2013.01)

(56) References Cited

U.S. PATENT DOCUMENTS

| | | |
|---|---|---|
| 1,385,346 A | 7/1921 | Taylor |
| 1,596,754 A | 8/1926 | Moschelle |
| 1,936,129 A | 11/1933 | Fisk |
| 2,195,771 A | 4/1940 | Estler |
| 2,221,758 A | 11/1940 | Elmquist |
| 2,338,339 A | 1/1944 | LaMere et al. |
| 2,443,481 A | 6/1948 | Sene |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans et al. |
| 3,026,874 A | 3/1962 | Stevens |
| 3,292,619 A | 12/1966 | Egler |
| 3,315,665 A | 4/1967 | MacLeod |
| 3,367,332 A | 2/1968 | Groves |
| 3,382,867 A | 5/1968 | Reaves |
| 3,520,300 A | 7/1970 | Flower, Jr. |
| 3,528,416 A | 9/1970 | Chamberlain |
| 3,568,675 A | 3/1971 | Harvey |
| 3,599,830 A | 8/1971 | Gilchrist et al. |
| 3,610,238 A | 10/1971 | Rich |
| 3,648,692 A | 3/1972 | Wheeler |
| 3,782,377 A | 1/1974 | Rychlik |
| 3,812,972 A | 5/1974 | Rosenblum |
| 3,814,095 A | 6/1974 | Lubens |
| 3,831,588 A | 8/1974 | Rindner |
| 3,874,387 A | 4/1975 | Barbieri |
| 3,903,882 A | 9/1975 | Augurt |
| 3,935,863 A | 2/1976 | Kliger |
| 3,954,105 A | 5/1976 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,178,974 A | 12/1979 | Levin |
| 4,191,204 A | 3/1980 | Nehring |
| 4,224,941 A | 9/1980 | Stivala |
| 4,250,882 A | 2/1981 | Adair |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,399,816 A | 8/1983 | Spangler |
| 4,457,755 A | 7/1984 | Wilson |
| 4,460,354 A | 7/1984 | Weilbacher et al. |
| 4,460,370 A | 7/1984 | Allison et al. |
| 4,465,062 A | 8/1984 | Versaggi et al. |
| 4,469,092 A | 9/1984 | Marshall et al. |
| 4,559,035 A | 12/1985 | Benjamin et al. |
| 4,608,041 A | 8/1986 | Nielsen |
| 4,624,656 A | 11/1986 | Clark et al. |
| 4,633,863 A | 1/1987 | Filips et al. |
| 4,637,819 A | 1/1987 | Ouellette et al. |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,717,382 A | 1/1988 | Clemens et al. |
| 4,733,659 A | 3/1988 | Edenbaum et al. |
| 4,740,202 A | 4/1988 | Stacey et al. |
| 4,743,232 A | 5/1988 | Kruger |
| 4,747,166 A | 5/1988 | Kuntz |
| 4,759,354 A | 7/1988 | Quarfoot |
| 4,765,316 A | 8/1988 | Marshall |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,834,110 A | 5/1989 | Richard |
| 4,872,450 A | 10/1989 | Austad |
| 4,886,502 A | 12/1989 | Poirier et al. |
| 4,897,081 A | 1/1990 | Poirier et al. |
| 4,906,240 A | 3/1990 | Reed et al. |
| 4,915,694 A | 4/1990 | Yamamoto et al. |
| 4,917,112 A | 4/1990 | Kalt |
| 4,921,492 A | 5/1990 | Schultz et al. |
| 4,930,997 A | 6/1990 | Bennett |
| 4,941,882 A | 7/1990 | Ward et al. |
| 4,953,565 A | 9/1990 | Tachibana et al. |
| 4,890,608 A | 10/1990 | Steer |
| 4,962,761 A | 10/1990 | Golden |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya et al. |
| 5,002,528 A | 3/1991 | Palestrant |
| 5,002,529 A | 3/1991 | Cunningham |
| 5,003,971 A | 4/1991 | Buckley |
| 5,014,389 A | 5/1991 | Ogilvie et al. |
| 5,034,003 A | 7/1991 | Denance |
| 5,034,006 A | 7/1991 | Hosoda et al. |
| 5,042,978 A | 8/1991 | Quenin et al. |
| 5,045,777 A | 9/1991 | Itagaki |
| 5,060,662 A | 10/1991 | Farnsworth, III |
| 5,071,409 A | 12/1991 | Rosenberg |
| 5,073,172 A | 12/1991 | Fell |
| 5,086,763 A | 2/1992 | Hathman |
| 5,086,764 A | 2/1992 | Gillman |
| 5,100,396 A | 3/1992 | Zamierowski |
| 5,101,808 A | 4/1992 | Kobayashi et al. |
| 5,106,362 A | 4/1992 | Gilman |
| 5,106,629 A | 4/1992 | Cartmell et al. |
| 5,135,518 A | 4/1992 | Vera |
| 5,147,338 A | 9/1992 | Lang et al. |
| 5,149,331 A | 9/1992 | Ferdman et al. |
| 5,152,757 A | 10/1992 | Eriksson |
| 5,160,322 A | 11/1992 | Scheremet et al. |
| 5,167,613 A | 12/1992 | Karami et al. |
| 5,170,781 A | 12/1992 | Loomis |
| 5,176,502 A | 1/1993 | Sanderson et al. |
| 5,176,663 A | 1/1993 | Svedman et al. |
| 5,176,667 A | 1/1993 | DeBring |
| 5,215,539 A | 6/1993 | Schoolman |
| 5,228,431 A | 7/1993 | Giarretto |
| 5,230,350 A | 7/1993 | Fentress |
| 5,238,654 A | 8/1993 | Nohl et al. |
| 5,261,893 A | 11/1993 | Zamierowski |
| 5,263,922 A | 11/1993 | Sova et al. |
| 5,291,887 A | 3/1994 | Stanley et al. |
| 5,298,015 A | 3/1994 | Komatsuzaki et al. |
| 5,330,452 A | 7/1994 | Zook |
| 5,344,415 A | 9/1994 | DeBusk et al. |
| 5,349,965 A | 9/1994 | McCarver |
| 5,358,494 A | 10/1994 | Svedman |
| 5,374,254 A | 12/1994 | Buma |
| 5,376,252 A | 12/1994 | Ekstrom et al. |
| 5,395,315 A | 3/1995 | Griep |
| 5,419,768 A | 5/1995 | Kayser |
| 5,431,622 A | 7/1995 | Pyrozyk et al. |
| 5,437,651 A | 8/1995 | Todd et al. |
| 5,445,604 A | 8/1995 | Lang |
| 5,451,215 A | 9/1995 | Wolter |
| 5,478,333 A | 12/1995 | Asherman, Jr. |
| 5,484,420 A | 1/1996 | Russo |
| 5,484,427 A | 1/1996 | Gibbons |
| 5,484,428 A | 1/1996 | Drainville et al. |
| 5,487,889 A | 1/1996 | Eckert et al. |
| 5,520,652 A | 5/1996 | Peterson |

(56) References Cited

U.S. PATENT DOCUMENTS

| | | | |
|---|---|---|---|
| 5,527,293 A | 6/1996 | Zamierowski |
| 5,531,670 A | 7/1996 | Westby et al. |
| 5,533,981 A | 7/1996 | Mandro et al. |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson et al. |
| 5,607,388 A | 3/1997 | Ewall |
| 5,624,418 A | 4/1997 | Shepard |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,660,350 A | 8/1997 | Byrne et al. |
| 5,662,598 A | 9/1997 | Tobin |
| 5,662,624 A | 9/1997 | Sundstrom et al. |
| 5,662,625 A | 9/1997 | Westwood |
| 5,669,892 A | 9/1997 | Keogh et al. |
| 5,672,152 A | 9/1997 | Mason et al. |
| 5,678,564 A | 10/1997 | Lawrence et al. |
| 5,690,815 A | 11/1997 | Krasnoff et al. |
| 5,697,920 A | 12/1997 | Gibbons |
| 5,735,833 A | 4/1998 | Olson |
| 5,741,237 A | 4/1998 | Walker |
| 5,755,706 A | 5/1998 | Kronenthal et al. |
| 5,759,570 A | 6/1998 | Arnold |
| 5,762,640 A | 6/1998 | Kajiwara et al. |
| 5,782,871 A | 7/1998 | Fujiwara et al. |
| 5,817,145 A | 10/1998 | Augustine et al. |
| 5,827,246 A | 10/1998 | Bowen |
| 5,911,222 A | 6/1999 | Lawrence et al. |
| 5,919,476 A | 7/1999 | Fischer et al. |
| 5,921,972 A | 7/1999 | Skow |
| 5,928,174 A | 7/1999 | Gibbins |
| 5,941,859 A | 8/1999 | Lerman |
| 5,947,914 A | 9/1999 | Augustine |
| 5,954,680 A | 9/1999 | Augustine |
| 5,961,480 A | 10/1999 | Augustine |
| 5,964,721 A | 10/1999 | Augustine |
| 5,964,723 A | 10/1999 | Augustine |
| 5,986,163 A | 11/1999 | Augustine |
| 6,010,527 A | 1/2000 | Augustine et al. |
| 6,017,493 A | 1/2000 | Cambron et al. |
| 6,039,724 A | 3/2000 | Seifert et al. |
| 6,045,518 A | 4/2000 | Augustine |
| 6,045,541 A | 4/2000 | Matsumoto et al. |
| 6,048,337 A | 4/2000 | Svedman |
| 6,056,730 A | 5/2000 | Greter |
| 6,071,254 A | 6/2000 | Augustine |
| 6,071,267 A | 6/2000 | Zamierowski |
| 6,071,304 A | 6/2000 | Augustine et al. |
| 6,080,189 A | 6/2000 | Augustine et al. |
| 6,080,243 A | 6/2000 | Insley et al. |
| 6,093,160 A | 7/2000 | Augustine et al. |
| 6,093,230 A | 7/2000 | Johnson, III et al. |
| 6,095,992 A | 8/2000 | Augustine |
| 6,110,197 A | 8/2000 | Augustine et al. |
| 6,113,561 A | 9/2000 | Augustine |
| 6,117,111 A | 9/2000 | Fleischmann |
| 6,135,116 A | 10/2000 | Vogel et al. |
| 6,142,982 A | 11/2000 | Hunt et al. |
| 6,143,945 A | 11/2000 | Augustine et al. |
| 6,165,994 A | 12/2000 | Henley |
| 6,174,306 B1 | 1/2001 | Fleischmann |
| 6,176,868 B1 | 1/2001 | Detour |
| 6,179,804 B1 | 1/2001 | Satterfield |
| 6,203,563 B1 | 3/2001 | Fernandez |
| 6,207,875 B1 | 3/2001 | Lindqvist et al. |
| 6,213,965 B1 | 4/2001 | Augustine et al. |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine et al. |
| 6,241,697 B1 | 6/2001 | Augustine |
| 6,241,698 B1 | 6/2001 | Augustine |
| 6,244,311 B1 | 6/2001 | Hand et al. |
| 6,244,698 B1 | 6/2001 | Hand et al. |
| 6,248,084 B1 | 6/2001 | Augustine et al. |
| 6,254,557 B1 | 7/2001 | Augustine et al. |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine et al. |
| 6,283,931 B1 | 9/2001 | Augustine |
| 6,284,941 B1 | 9/2001 | Cox et al. |
| 6,290,685 B1 | 9/2001 | Insley et al. |
| 6,293,917 B1 | 9/2001 | Augustine et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,468,237 B1 | 10/2002 | Lina |
| 6,491,682 B2 | 12/2002 | Paderni |
| 6,645,226 B1 | 11/2003 | Jacobs et al. |
| 6,648,862 B2 | 11/2003 | Watson |
| 6,663,349 B1 | 12/2003 | Discenzo et al. |
| 6,685,681 B2 | 2/2004 | Anker et al. |
| 6,691,047 B1 | 2/2004 | Fredericks |
| 6,695,823 B1 | 2/2004 | Lina et al. |
| 6,749,592 B2 | 6/2004 | Lord |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,824,533 B2 | 11/2004 | Risk, Jr. et al. |
| 6,855,135 B2 | 2/2005 | Lockwood et al. |
| 6,893,452 B2 | 5/2005 | Jacobs |
| 6,978,816 B1 | 12/2005 | Byrne et al. |
| 6,978,884 B2 | 12/2005 | Lockwood |
| 7,004,915 B2 | 2/2006 | Boynton et al. |
| 7,022,113 B2 | 4/2006 | Lockwood et al. |
| 7,108,683 B2 | 9/2006 | Zamierowski |
| 7,117,869 B2 | 10/2006 | Heaton et al. |
| 7,128,795 B2 | 10/2006 | Byrne et al. |
| 7,156,862 B2 | 1/2007 | Jacobs et al. |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,276,051 B1 | 10/2007 | Henley et al. |
| 7,338,482 B2 | 3/2008 | Lockwood et al. |
| 7,361,184 B2 | 4/2008 | Joshi |
| 7,381,211 B2 | 6/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,520,872 B2 | 4/2009 | Biggie et al. |
| 7,524,286 B2 | 4/2009 | Johnson |
| 7,524,315 B2 | 4/2009 | Blott et al. |
| 7,532,953 B2 | 5/2009 | Vogel |
| 7,534,927 B2 | 5/2009 | Lockwood et al. |
| 7,608,066 B2 | 10/2009 | Vogel |
| 7,645,269 B2 | 1/2010 | Zamierowski |
| 7,651,484 B2 | 1/2010 | Heaton et al. |
| 7,678,090 B2 | 3/2010 | Risk, Jr. et al. |
| 7,723,560 B2 | 5/2010 | Lockwood et al. |
| 7,763,000 B2 | 7/2010 | Risk, Jr. et al. |
| 7,794,438 B2 | 9/2010 | Henley et al. |
| 7,837,673 B2 | 11/2010 | Vogel |
| 7,867,206 B2 | 1/2011 | Lockwood et al. |
| 7,883,494 B2 | 2/2011 | Martin |
| 7,896,864 B2 | 3/2011 | Lockwood et al. |
| 7,922,703 B2 | 4/2011 | Riesinger |
| 7,927,318 B2 | 4/2011 | Risk, Jr. et al. |
| 7,927,352 B2 | 4/2011 | Wilke et al. |
| 7,951,100 B2 | 5/2011 | Hunt et al. |
| 7,967,810 B2 | 6/2011 | Freedman |
| 7,927,362 B2 | 7/2011 | Wilke et al. |
| 7,988,680 B2 | 8/2011 | Lockwood et al. |
| 8,057,446 B2 | 11/2011 | Kane et al. |
| 8,066,243 B2 | 11/2011 | Svedman et al. |
| 8,084,664 B2 | 12/2011 | Johnson et al. |
| 8,142,405 B2 | 3/2012 | Vogel |
| 8,162,909 B2 | 4/2012 | Blott et al. |

(56) References Cited

U.S. PATENT DOCUMENTS

| | | |
|---|---|---|
| 8,168,848 B2 | 5/2012 | Lockwood et al. |
| 8,187,210 B2 | 5/2012 | Hunt et al. |
| 8,350,116 B2 | 1/2013 | Lockwood et al. |
| 8,372,049 B2 | 2/2013 | Jaeb et al. |
| 8,376,972 B2 | 2/2013 | Fleischmann |
| 8,425,478 B2 | 4/2013 | Olson |
| 8,444,613 B2 | 5/2013 | Svedman et al. |
| 8,447,375 B2 | 5/2013 | Freedman et al. |
| 8,460,258 B2 | 6/2013 | Jones et al. |
| 8,460,273 B2 | 6/2013 | Freedman et al. |
| 8,974,428 B2 | 3/2015 | Freedman |
| 9,393,354 B2 | 7/2016 | Freedman et al. |
| 10,058,643 B2 | 8/2018 | Freedman et al. |
| 10,149,930 B2 | 12/2018 | Freedman |
| 10,258,270 B2 | 4/2019 | Freedman |
| 10,485,906 B2 | 11/2019 | Freedman |
| 11,766,514 B2 * | 9/2023 | Shuler ............... A61M 1/90 604/305 |
| 2001/0031943 A1 | 10/2001 | Urie |
| 2002/0065494 A1 | 5/2002 | Lockwood et al. |
| 2002/0115967 A1 | 8/2002 | Svedman |
| 2002/0143286 A1 | 10/2002 | Tumey |
| 2002/0150720 A1 | 10/2002 | Howard et al. |
| 2002/0161346 A1 | 10/2002 | Lockwood |
| 2002/0183702 A1 | 12/2002 | Henley |
| 2003/0050594 A1 | 3/2003 | Zamierowski |
| 2003/0139255 A1 | 7/2003 | Lina |
| 2003/0163160 A1 | 8/2003 | O'Malley et al. |
| 2003/0208149 A1 | 11/2003 | Coffey |
| 2004/0006319 A1 | 1/2004 | Lina et al. |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0243073 A1 | 12/2004 | Lockwood et al. |
| 2004/0265040 A1 | 12/2004 | Rosenberg |
| 2005/0070858 A1 | 3/2005 | Lockwood et al. |
| 2005/0085795 A1 | 4/2005 | Lockwood |
| 2006/0041238 A1 | 2/2006 | Bowen |
| 2006/0065494 A1 | 3/2006 | Kim |
| 2006/0129137 A1 | 6/2006 | Lockwood et al. |
| 2006/0155260 A1 | 7/2006 | Blott et al. |
| 2006/0282028 A1 | 12/2006 | Howard et al. |
| 2007/0038247 A1 | 2/2007 | Lebner et al. |
| 2007/0167926 A1 | 7/2007 | Blott et al. |
| 2007/0225634 A1 | 9/2007 | Ferren et al. |
| 2007/0225663 A1 | 9/2007 | Watt et al. |
| 2007/0233022 A1 | 10/2007 | Henley et al. |
| 2008/0041401 A1 | 2/2008 | Casola et al. |
| 2008/0167593 A1 | 7/2008 | Fleischmann |
| 2008/0208011 A1 | 8/2008 | Shuler |
| 2008/0300555 A1 * | 12/2008 | Olson ............... A61F 13/05 604/313 |
| 2009/0012482 A1 | 1/2009 | Pinto et al. |
| 2009/0082740 A1 | 3/2009 | Lockwood et al. |
| 2009/0177051 A1 | 7/2009 | Arons et al. |
| 2009/0221977 A1 | 9/2009 | Blott et al. |
| 2010/0049151 A1 | 2/2010 | Aicher |
| 2010/0057022 A1 | 3/2010 | Horrigan |
| 2010/0063483 A1 | 3/2010 | Adahan |
| 2010/0069885 A1 | 3/2010 | Stevenson |
| 2010/0160876 A1 | 6/2010 | Robinson et al. |
| 2010/0160877 A1 | 6/2010 | Kagan et al. |
| 2010/0174250 A1 | 7/2010 | Hu |
| 2010/0185236 A1 | 7/2010 | Elliott et al. |
| 2010/0191196 A1 | 7/2010 | Heagle |
| 2010/0191198 A1 | 7/2010 | Heagle |
| 2010/0262091 A1 | 10/2010 | Larsson |
| 2010/0280428 A1 | 11/2010 | Widgerow et al. |
| 2010/0292549 A1 | 11/2010 | Shuler |
| 2011/0034888 A1 | 2/2011 | Aali |
| 2011/0054283 A1 | 3/2011 | Shuler |
| 2011/0106026 A1 | 5/2011 | Wu et al. |
| 2011/0125110 A1 | 5/2011 | Cotton |
| 2011/0172617 A1 | 7/2011 | Riesinger |
| 2011/0213319 A1 | 9/2011 | Blott et al. |
| 2012/0041403 A1 | 2/2012 | Bennett et al. |
| 2012/0143114 A1 * | 6/2012 | Locke ............... A61F 13/01017 604/319 |
| 2012/0143122 A1 * | 6/2012 | Ruiz Soto ............... A61M 1/92 604/93.01 |
| 2012/0316518 A1 | 12/2012 | Croizt et al. |
| 2013/0096520 A1 | 4/2013 | Lockwood et al. |
| 2013/0138060 A1 | 5/2013 | Haggstrom et al. |
| 2013/0144230 A1 | 6/2013 | Wu et al. |
| 2013/0165821 A1 | 6/2013 | Freedman et al. |
| 2013/0165878 A1 | 6/2013 | Heagle |
| 2013/0172834 A1 | 7/2013 | Heagle |
| 2013/0274695 A1 | 10/2013 | Freedman et al. |
| 2014/0018752 A1 | 1/2014 | Shuler et al. |
| 2014/0052083 A1 | 2/2014 | Freedman |
| 2014/0066868 A1 | 3/2014 | Freedman |
| 2014/0221907 A1 | 8/2014 | Scholz |
| 2015/0190288 A1 | 7/2015 | Dunn |
| 2015/0320434 A1 | 11/2015 | Ingram et al. |
| 2016/0120706 A1 | 5/2016 | Collinson et al. |
| 2017/0028113 A1 | 2/2017 | Shuler |
| 2017/0224889 A1 | 8/2017 | Robinson et al. |
| 2018/0353334 A1 | 12/2018 | Locke et al. |
| 2019/0111192 A1 | 4/2019 | Freedman |
| 2019/0117465 A1 | 4/2019 | Osborne |
| 2019/0240383 A1 | 8/2019 | Freedman |
| 2019/0262181 A1 | 8/2019 | Long et al. |
| 2019/0343687 A1 | 11/2019 | Locke et al. |

FOREIGN PATENT DOCUMENTS

| | | |
|---|---|---|
| CA | 2789685 | 9/2011 |
| CA | 2879108 | 1/2014 |
| CN | 103623496 | 3/2014 |
| EP | 1304966 | 5/2003 |
| EP | 2815731 | 12/2014 |
| WO | WO 1997005838 | 2/1997 |
| WO | WO 2003057070 | 7/2003 |
| WO | WO 2006114648 | 11/2006 |
| WO | WO 2007041642 | 4/2007 |
| WO | WO 2008106396 | 4/2008 |
| WO | WO 2008100440 | 8/2008 |
| WO | WO 2009062327 | 5/2009 |
| WO | WO 2009093116 | 7/2009 |
| WO | WO 2009141820 | 11/2009 |
| WO | WO 2010129528 | 11/2010 |
| WO | WO 2011091045 | 7/2011 |
| WO | WO 2013066694 | 5/2013 |
| WO | WO 2017063036 | 4/2017 |
| WO | WO 2018226664 | 12/2018 |
| WO | WO 2019136164 | 7/2019 |

OTHER PUBLICATIONS

Argenta et al., "Vacuum-Assisted Closure: A New Method For Wound Control And Treatment: Basic Foundation," Annals Of Plastic Surgery, 1997, 38(6): 553-562.

Argenta et al., "Vacuum-Assisted Closure: A New Method For Wound Control And Treatment: Clinical Experience," Annals of Plastic Surgery, 1997, 38(6): 563-577.

Barker et al., "Vacuum pack technique of temporary abdominal closure: a 7-year experience with 112 patients," J Trauma, Feb. 2000, 48(2): 201-6.

Barnea et al., "Our experience with Wisebands: a new skin and soft-tissue stretch device," Plast Reconstr Surg, Mar. 2004, 113(3): 862-9.

Brock et al., "Temporary Closure of Open Abdominal Wounds: The Vacuum Pack," Am Surg., 1995, 61(1): 30-35.

Buckman, "Vacuum Assisted Wound Closure System," Drexel University white paper, Jul. 15, 2006.

Campbell, "Surgical wound case studies with the versatile 1 wound vacuum system for negative pressure wound therapy," J Wound Ostomy Continence Nurs, Mar. 2006, 33(2): 176-85.

Chariker et al., "An algorithmic approach to the use of gauze-based negative-pressure wound therapy as a bridge to closure in pediatric extremity trauma," Plast Reconstr Surg, May 2009, 123(5): 1510-20.

(56) References Cited

OTHER PUBLICATIONS

Chariker et al., "Effective management of incisional and cutaneous fistulae with closed suction wound drainage," Contemp Surg 1989;34:59-63.
Conde-Green, et al., "Incisional Negative-Pressure Wound Therapy Versus Conventional Dressings Following Abdominal Wall Reconstruction: A Comparative Study," Ann. Plast. Surg., 2013, 71:394-397.
Davydov et al., "Concepts for Clinical Biological Management of the Wound Process in the Treatment of Purulent Wounds Using Vacuum Therapy," The Kremlin Papers; Perspectives in Wound Care from the Russian Medical Journal, 1991, 132-135.
Davydov et al., "The Bacteriological and Cytological Assessment of Vacuum Therapy of Purulent Wounds," The Kremlin papers, Perspectives in Wound Care from the Russian Medical Journal, 1988, 48-52.
Davydov et al., "Vacuum Therapy in the Treatment of Purulent lactation Mastitis," The Kremlin papers, perspectives in Wound Care from the Russian Medical Journal, 1986, 66-70.
Extended European Search Report in European Appln No. 21743873.8, dated Dec. 16, 2022, 7 pages.
Giovinco et al., "Wound chemotherapy by the use of negative pressure wound therapy and infusion," Eplasty, Jan. 2010, 8(10): e9, 8 pages.
Jeter, "Closed suction wound drainage system," J Wound Ostomy Continence Nurs, Mar. 2004, 31(2): 51.
Kostiuchenok et al., "The Vacuum Effect in the Surgical Treatment of Purulent Wounds," The Kremlin Papers, Perspectives in Wound Care from the Russian Medical Journal, 1986, 18-21.
Leininger et al., "Experience with wound VAC and delayed primary closure of contaminated soft tissue injuries in Iraq," J Trauma, Nov. 2006, 61(5): 1207-11.
Miller et al., "Negative pressure wound therapy: An option for hard-to-heal wounds," J Wound Care 2006, 15(7):321-324.
Morykwas et al., "Vacuum-Assisted Closure: A New Method For Wound Control And Treatment: Basic Foundation," Annals Of Plastic Surgery, 1997, 38(6): 553-562.
Morykwas et al., "Vacuum-assisted closure: state of basic research and physiologic foundation," Plast Reconstr Surg, Jun. 2006, 117(7 Suppl): 121S-126S.
Navsaria et al., "Temporary closure of open abdominal wounds by the modified sandwich-vacuum pack technique," Br J Surg, Jun. 2003, 90(6): 718-22.
Nguyen, et al., "Prospective Randomized Controlled Trial Comparing Two Methods of Securing Skin Grafts Using Negative Pressure Wound Therapy: Vacuum-Assisted Closure and Gauze Suction," J. Burn Care Res., 2015, 36:324-328.
PCT International Search Report and Written Opinion in International Appln. No. PCT/US2021/14608, dated May 24, 2021, 13 pages.
Perez et al., "Modern wound care for the poor: a randomized clinical trial comparing the vacuum system with conventional saline-soaked gauze dressings," The American Journal of Surgery, 2010, 199: 14-20.
Pliakos et al., "Vacuum-assisted closure in severe abdominal sepsis with or without retention sutured sequential fascial closure: a clinical trial," Surgery, Nov. 2010, 148(5): 947-53.
Polymer Science, Inc., "P-Derm Hydrogels," Nov. 29, 2014, Retrieved from the Internet on Dec. 29, 2016: URL: <https://web.archive.org/web/20141129100425/http://www.polymerscience.com/products/hydrogel/>, 2 pages.
Psoinos, et al., "Use of gauze-based negative pressure wound therapy in a pediatric burn patient," J. Pediatric Surgery, 2009, 44:E23-E26.
Scherer et al., "The vacuum assisted closure device: A method for securing skin grafts and improving graft survival," Arch Surg., 2002, 137(8): 930-933.
Singh et al., "Dynamic Wound Closure for Decompressive Leg Fasciotomy Wounds," Am Surg, 2008, 74(3): 217-220.
Svedman et al., "A dressing system providing fluid supply and suction drainage used for continuous or intermittent irrigation," Ann Plast Surg, Aug. 1986, 17(2): 125-33.
Thai et al., "Ultraviolet light C in the treatment of chronic wounds with MRSA: a case study," Ostomy Wound Manage, Nov. 2002, 48(11): 52-60.
Thomas, "Silicones in Medical Applications," Dow Coring Europe SA, Sep. 8, 2011, Retrieved from the Internet on Dec. 29, 2016: URL:<https://web.archive.org/web/20110908185846/http://www.dowcorning.com/content/publishedlit/Chapter17.pdf>, 9 pages.
Usupov et al., "Active Wound Drainage," The Kremlin Papers, Perspectives in Wound Care from the Russian Medical Journal, 1987, 42-45.
Utz et al., "Metalloproteinase expression is associated with traumatic wound failure," J Surg Res, Apr. 2010, 159(2): 633-9.
Valenta, "Using the Vacuum Dressing Alternative for Difficult Wounds," American J. of Nursing, 1994, 44-45.
Van der Velde and Hudson, "VADER (vacuum-assisted dermal recruitment: a new method of wound closure," Annals of Plastic Surgery, 2005, 55(6): 660-664.
Wackenfors, et al., "Effects of vacuum-assisted closure therapy on inguinal wound edge microvascular blood flow," Wound Repaire and Regeneration, 2004, 12(6): 600-606.
Webb, "New Techniques in Wound Management: Vacuum-assisted Wound Closure," J. Am Acad Orthop Surg, 2002, 10(5): 303-311.
Webster, et al., "Negative pressure wound therapy for skin gra s and surgical wounds healing by primary intention," Cochrane Database of Systematic Reviews, 2014, 10:CD0009261, 3 pages.
Wolvos, "Wound instillation—the next step in negative pressure wound therapy. Lessons learned from initial experiences.," Ostomy Wound Manage, Nov. 2004, 50(11): 56-66.
Zannis et al, "Comparison of Fasciotomy Wound Closures Using Traditional Dressing Changes and the Vacuum-assisted Closure Device," Annals of Plastic Surgery, 2009, 62(4): 407-409.
Zorilla, et al., "Shoelace technique for gradual closure of fasciotomy wounds," The Journal of Trama, 2005, 59(6): 1515-1517.

* cited by examiner

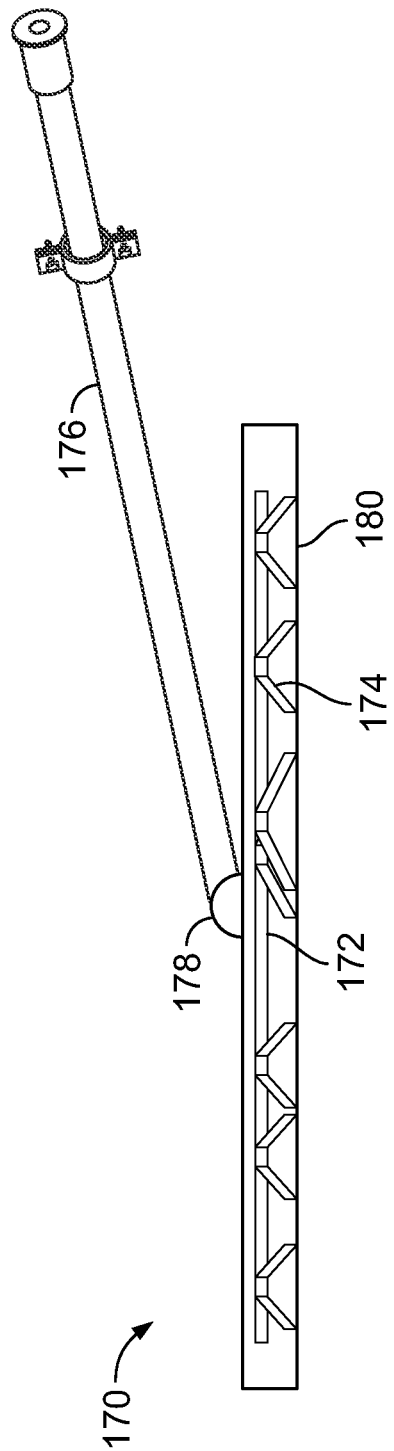

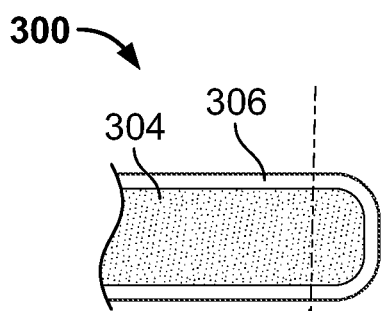
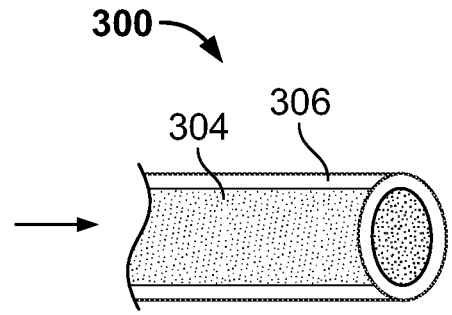
FIG. 10A  FIG. 10B
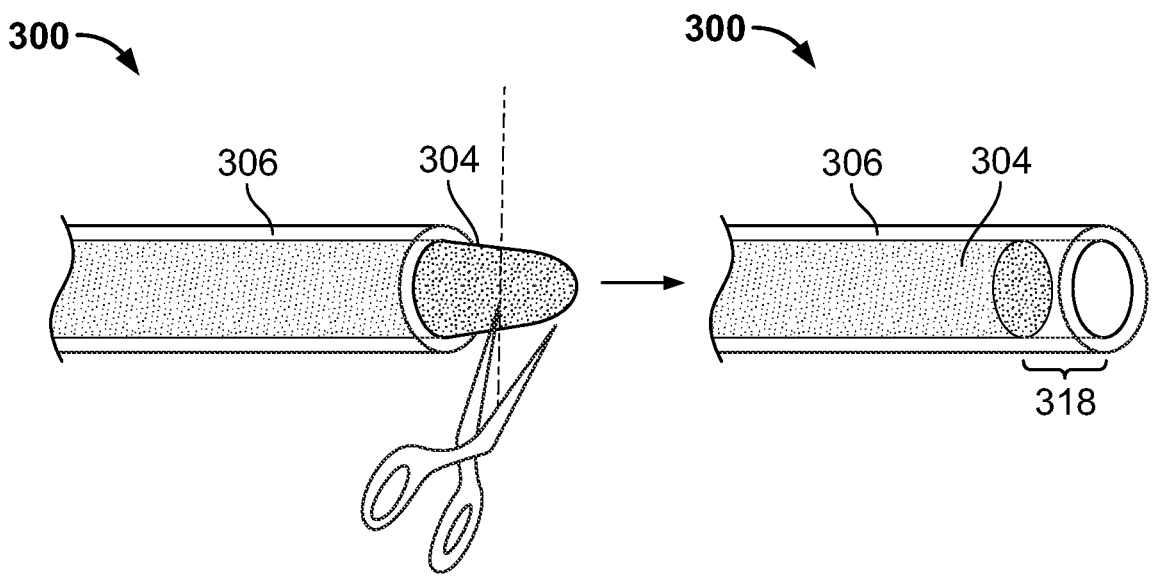
FIG. 10C  FIG. 10D

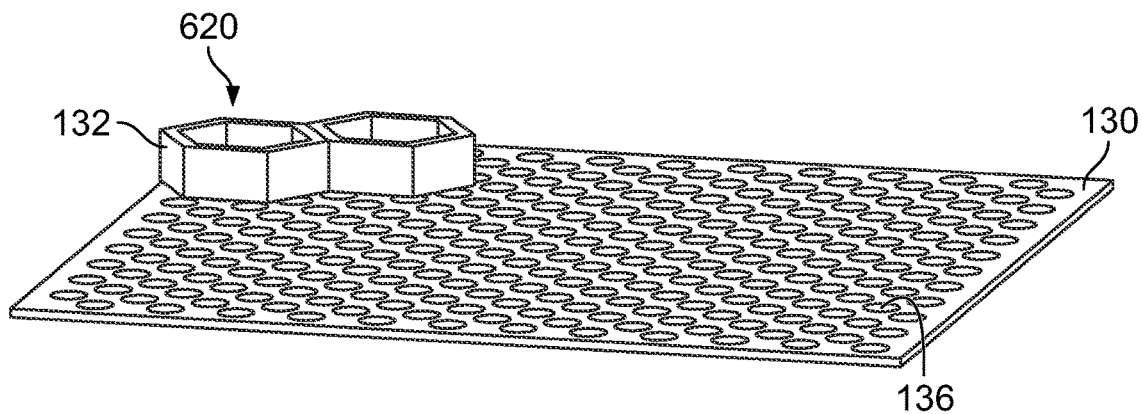
FIG. 16A
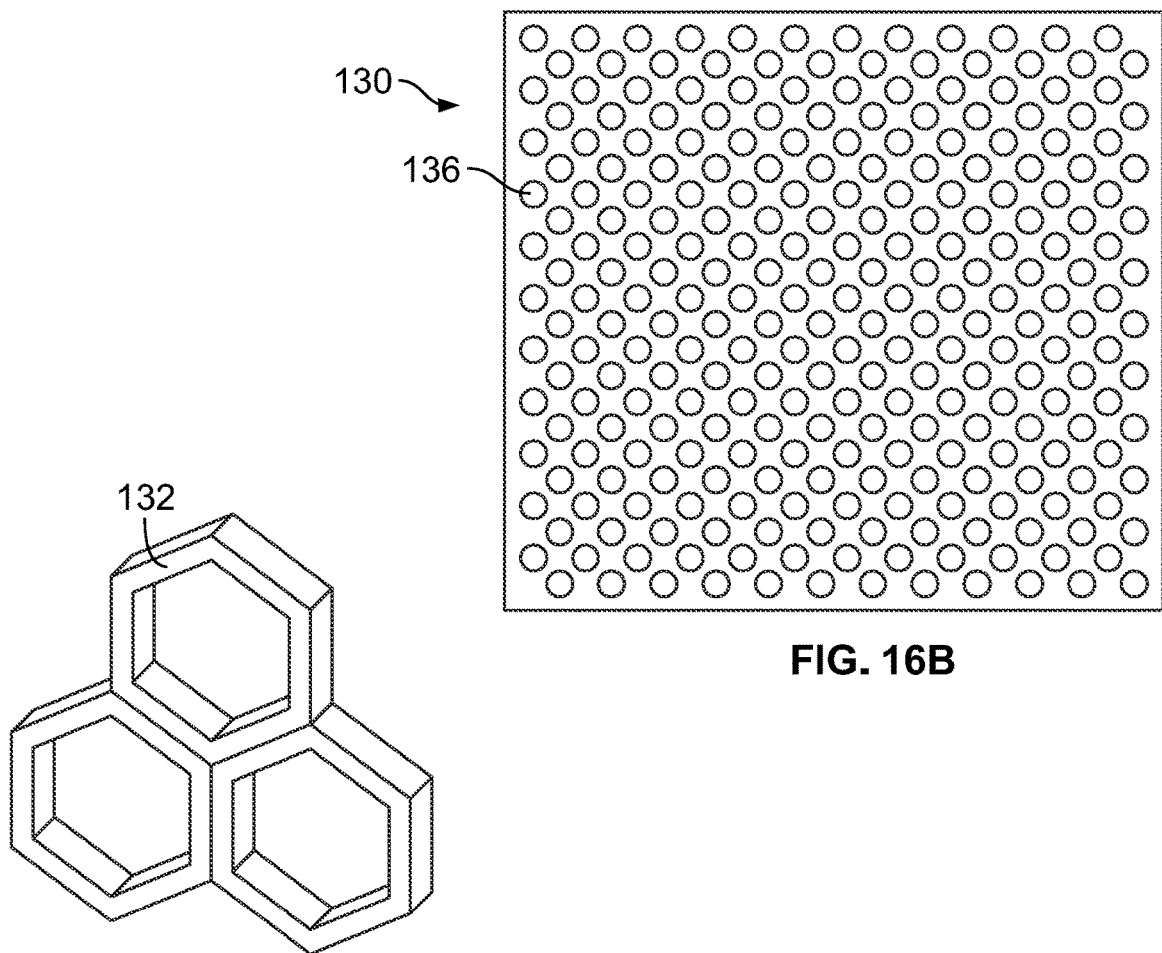
FIG. 16B
FIG. 16C

BARRIER TO PREVENT OR REDUCE INGROWTH OF TISSUE

CROSS-REFERENCE TO RELATED APPLICATIONS

This application is a continuation of U.S. application Ser. No. 17/515,896, filed on Nov. 1, 2021, which is a continuation of U.S. application Ser. No. 16/749,511, filed on Jan. 22, 2020, now U.S. Pat. No. 11,160,917. The disclosure of the prior application is considered part of (and is incorporated by reference in) the disclosure of this application.

TECHNICAL FIELD

The present invention relates to patient wound care, and more specifically to systems and methods of wound coverings and dressings.

BACKGROUND

Negative-pressure wound therapy (NPWT) is a type of treatment used by physicians to promote the healing of acute or chronic wounds. For example, sealed wound dressings connected to a vacuum pump can be placed onto an open wound for applying sub-atmospheric pressure to the wound. Such types of negative-pressure applications can be used to draw out fluid from the wound and increase blood flow to a wound area.

SUMMARY

Some embodiments include methods and systems for use in negative pressure wound therapy (NPWT). A barrier can be configured to be positioned adjacent to wound tissue and prevent or reduce tissue ingrowth from the wound tissue into a pad positioned above the barrier. The barrier can have structures configured to allow for fluid flow yet still inhibit tissue ingrowth. The barrier can be provided separately from existing NPWT dressings and/or used with the existing NPWT dressing to improve performance. The barrier can include irrigation flow channels to allow for simultaneous irrigation and NPWT. The barrier can include one or more other features described herein.

In some implementations, a method of using a negative pressure wound therapy system includes providing or receiving a wound dressing comprising a pad and a membrane, wherein the pad is porous, wherein the pad and the membrane are configured to be used for negative pressure wound therapy, providing or receiving a barrier, wherein the barrier is provided separately from the wound dressing, wherein the barrier includes a plurality of perforations, wherein the barrier is configured to be positioned in a wound adjacent to wound tissue, and wherein the barrier is configured to prevent or reduce tissue ingrowth from the wound tissue into the pad, and positioning the barrier in the wound adjacent to the wound tissue. After positioning the barrier in the wound, the pad can be positioned in the wound on top of the barrier in a location that is spaced from the wound tissue by the barrier, the seal can be positioned on top of the pad and wound to at least partially seal the barrier and the pad in the wound, and negative pressure wound therapy can be applied to the wound while the pad and the barrier are positioned in the wound such that fluid is allowed to flow from the wound tissue, through the perforations of the barrier, through the pores of the pad, and through an outlet of the wound dressing.

Implementations can include any, all, or none of the following features. The pad may be an open cell foam sponge, wherein the barrier is an injection molded polymer barrier having complex geometry that is configured to space the open cell foam sponge material from the wound tissue to reduce or prevent tissue ingrowth. The barrier comprises a base layer and a plurality of walls extending from the base layer, wherein a first plurality of the perforations are positioned so as to extend through the base layer at positions between the walls, and wherein a second plurality of perforations are positioned so as to extend through the base layer at positions under the walls. The walls form a repeating polygonal shape, wherein the walls meet at wall intersections, and wherein the second plurality of perforations are positioned under the walls at some but not all of the wall intersections. The walls have a greater height at locations where the walls connect to the base layer than at locations which have the second plurality of perforations positioned under the walls. The barrier comprises a base layer and a plurality of walls extending from the base layer, wherein the walls form a repeating polygonal shape, and wherein posts extend from the base layer at indentations defined between the walls. The barrier comprises a base layer and a plurality of walls extending from top and bottom sides of the base layer, wherein the barrier comprises a plurality of tabs extending from the top side of the base layer, wherein the tabs are configured to be grabbed to pull the barrier out of the wound. The method can further include sucking liquid and exudate through the perforations of the barrier, removing the wound dressing, including removing the pad and the membrane, from the wound, and after removing the wound dressing, removing the barrier from the wound by grabbing one or more tabs extending from the barrier with a tool or one's fingers and pulling. The barrier comprises an injection molded polymer, a radiopaque marker positioned in the injection molded polymer, and a coating positioned on an outer surface of the polymer. The pad is an open cell foam sponge, wherein the barrier is a polymer barrier having complex geometry that is configured to space the wound tissue from the perforations of the barrier, wherein the barrier is integrally formed as a single piece. The barrier is designed to be used with the wound dressing and wherein the wound dressing is designed to be used without the barrier. The barrier has a width that is multiple centimeters long, wherein the barrier has a length that is multiple centimeters long, wherein the barrier has a thickness that is 1 to 5 mm thick, and wherein the perforations extending through the barrier have a 1 to 5 mm diameter. The plurality of perforations extend through a base layer of the barrier and wherein the barrier defines structure at least partially blocking the perforations. The method can further include cutting the pad to a pad size suitable to be placed in the wound and cutting the barrier to a barrier size suitable to be placed in the wound, wherein the pad and the barrier are cut separately in separate steps.

In some implementations, a method of using a negative pressure wound therapy system includes positioning a perforated barrier in a wound. After positioning the perforated barrier in the wound, positioning a pad in the wound on top of the perforated barrier, positioning a seal on top of the wound to at least partially seal the perforated barrier and the pad in the wound, and applying negative pressure wound therapy to the wound.

In some implementations, a barrier for use in negative pressure wound therapy includes a base layer and top surface structures. The base layer defines a plurality of perforations through the base layer, wherein the plurality of perforations are positioned, sized, and configured to allow flow therethrough for negative pressure wound therapy, wherein the base layer defines a top surface and a bottom surface. The top surface structures are positioned on the top surface of the base layer, wherein the top surface structures are positioned, sized, and configured to space porous foam material away from the perforations of the base layer when porous foam material is positioned on top of the barrier after the barrier is positioned in the wound.

Implementations can include any, all, or none of the following features. The barrier has a thickness and a structure configured to create a physical separation between the pad and reduce or prevent tissue ingrowth through the perforations to a porous foam material positioned above the barrier. The top surface structures comprise walls forming a repeating geometric shape, and wherein the walls at least partially cover and block at least some of the perforations through the base layer. The top surface structure comprises walls forming a repeating geometric shape, posts positioned between the walls, and tabs extending upward from the walls. The base layer and the top surface structures comprise a pliable medical grade polymer and further comprising filaments or radiopaque markers embedded in the pliable medical grade polymer. The barrier defines a first set of irrigation channels and a second set of irrigation channels, wherein a plurality of irrigation channels from the second set of irrigation channels branch out from each of the irrigation channels in the first set of irrigation channels. The barrier defines an inlet along an edge of the barrier, wherein the inlet is fluidly connected to the first set of irrigation channels and the second set of irrigation channels with the first set of irrigation channels positioned between the inlet and the second set of irrigation channels. This inlet can extend normal to the surface of the barrier, to pass through and overlying pad and connect to an irrigation source. The barrier defines an inlet at a middle portion of the barrier, wherein the inlet is fluidly connected to the first set of irrigation channels and the second set of irrigation channels with the first set of irrigation channels positioned between the inlet and the second set of irrigation channels.

In some implementations, a negative pressure wound therapy system includes a wound dressing comprising a membrane, a pad comprising a porous foam sponge configured to be positioned under the membrane, and a barrier configured to be positioned under the pad. The barrier includes a plurality of perforations, wherein the pad and the barrier are configured to be positioned together in a wound with the barrier positioned adjacent to wound tissue and the pad positioned between the barrier and the membrane, and wherein the barrier is configured to prevent or reduce tissue ingrowth from the wound tissue into the pad.

Implementations can include any, all, or none of the following features. The pad is an open cell foam sponge, wherein the barrier is an injection molded or otherwise fabricated polymer barrier having complex geometry that is configured to space the open cell foam sponge material from the wound tissue to prevent tissue ingrowth. The barrier comprises a base layer and a plurality of walls extending from the base layer, wherein a first plurality of the perforations are positioned so as to extend through the base layer at positions between the walls, and wherein a second plurality of perforations are positioned so as to extend through the base layer at positions under the walls. The barrier comprises a base layer and a plurality of walls extending from the base layer, wherein the walls form a repeating polygonal shape, and wherein posts extend from the base layer at indentations defined between the walls. The barrier comprises an injection molded polymer, a radiopaque marker positioned in the injection molded polymer, and a coating positioned on an outer surface of the polymer. The plurality of perforations extend through a base layer of the barrier and the barrier defines structure at least partially blocking the perforations. The barrier is physically attached to the pad so as to be sold and delivered together. The barrier is attachable to the pad via one or more fasteners. The barrier defines a first set of irrigation channels and a second set of irrigation channels, wherein a plurality of irrigation channels from the second set of irrigation channels branch out from each of the irrigation channels in the first set of irrigation channels.

In some implementations, a barrier for use in negative pressure wound therapy and wound irrigation includes a base layer defining a plurality of perforations through the base layer, wherein the plurality of perforations are positioned, sized, and configured to allow flow therethrough for negative pressure wound therapy, wherein the base layer defines a top surface and a bottom surface. The barrier defines a first set of irrigation channels and a second set of irrigation channels, wherein a plurality of irrigation channels from the second set of irrigation channels branch out from each of the irrigation channels in the first set of irrigation channels. The perforations of the barrier are sized, positioned, and configured to allow for suction flow from a wound surface positioned under the bottom surface of the base layer, through the perforations, and to an area above the top surface of the base layer. The first and second sets of irrigation channels of the barrier are sized, positioned, and configured to allow for irrigation through the first and second sets of irrigation channels to the wound surface. The barrier is configured to allow for the suction and the irrigation simultaneously.

Implementations can include any, all, or none of the following features. The barrier defines an inlet along an edge of the barrier, wherein the inlet is fluidly connected to the first set of irrigation channels and the second set of irrigation channels with the first set of irrigation channels positioned between the inlet and the second set of irrigation channels. The barrier defines an additional irrigation channel extending from the inlet to the second set of irrigation channels so as to fluidly connect the inlet to the first set of irrigation channels. The barrier defines an inlet at a middle portion of the barrier, wherein the inlet is fluidly connected to the first set of irrigation channels and the second set of irrigation channels with the first set of irrigation channels positioned between the inlet and the second set of irrigation channels. The inlet tube is of sufficient length to more than traverse the full thickness of the pad overlying the barrier, whether the pad is placed piece-meal as a separate unit during dressing application or is manufactured to be fixedly attached to the barrier as a single unit. The inlet tube will also penetrate the sealing membrane after complete application of the dressing and then connect to an irrigation supply tubing which communicates the irrigant from the irrigation source to the dressing. The point at which the inlet tube will penetrate or cross the sealing membrane can be further improved, by including an integrated flat manifold, which acts to hold the inlet tubing, generally normal to the dressing in a central location, and further provide a flat surface where the sealing membrane can be adhered at application of the dressing to the body. This flat surface allows for easier application of the sealing membrane encouraging an airtight seal for the dressing, which is a preferred state. This manifold can also include a separate attachment point or coupling for the suction tubing that extends from the regulated vacuum source to the dressing. The barrier further comprises top surface structures positioned on the top surface of the base layer, wherein the top surface structures are positioned, sized, and configured to space porous foam material away from the perforations of the base layer when porous foam material is positioned on top of the barrier after the barrier is positioned in the wound. The second set of irrigation channels terminate at outlets that are positioned at the bottom surface of the barrier, wherein some of the outlets are positioned proximate a perimeter of the barrier with other outlets positioned closer to a center of the barrier. A tubular extension extends from the inlet in a direction that is generally normal to the barrier. A system includes the barrier, a wound dressing comprising a pad with the barrier fixedly attached to the pad, and a tubular extension that extends from the irrigation inlet of the barrier through the pad to an end that is configured to be connected to an irrigation source. The tubular extension is configured to allow for simultaneous irrigation and negative pressure. The tubular extension is configured to allow for alternating irrigation and negative pressure. A manifold is fluidically connected to the tubular extension. The manifold is positioned adjacent the pad at a location where the tubular extension extends through the pad. The manifold defines a suction inlet configured to connect to suction tubing.

In some implementations, a system includes a wound dressing comprising a membrane, a pad, and a barrier. The pad comprises a porous foam sponge configured to be positioned under the membrane. The pad comprises a pad bottom, a pad top, and pad sides. The barrier is wrapped around the pad, wherein the barrier is configured to prevent or reduce tissue ingrowth from the wound tissue into the pad.

Implementations can include any, all, or none of the following features. The barrier is wrapped around a pad bottom and at least part of the pad sides. The barrier is wrapped around a circumference of the pad. The barrier is wrapped completely around a circumference of the pad. The barrier and the pad are sized and shaped to be used in fistulous or tunneled wounds that have a long narrow geometry. The pad comprises a sponge. The barrier comprised medical grade polymer The barrier defines perforations. The pad and barrier combine to form a shape that is long and narrow at a distal end and wider and flatter at a proximal end. The barrier is substantially nail shaped. The barrier is substantially funnel shaped. The barrier is substantially kettle shaped. The barrier comprises a head portion and a cylinder portion The cylinder portion is perforated. The cylinder portion is wrapped around the pad sides. The wound dressing comprises one or more irrigation flow paths configured to deliver irrigant to the barrier. The wound dressing comprised one or more suction flow paths configured to provide negative pressure at the dressing. The one or more irrigation flow paths are independent from the one or more suction flow paths. A method of using the wound dressing includes cutting a distal end of the wound dressing so as to cut both the pad and the barrier. The pad can be moved at least partially out of the distal end of the wound dressing. A portion of the pad that was pulled out of the distal end of the wound dressing can be cut. The pad can be moved back into the wound dressing. The pad can be positioned inside the barrier such that the pad is spaced inward from a distal opening of the barrier by a gap. A distal opening of the barrier can be closed after the barrier has been cut. A distal opening of the barrier can be sutured after the barrier has been cut.

Other features, aspects and potential advantages will be apparent from the accompanying description and figures.

BRIEF DESCRIPTION OF THE DRAWINGS

FIGS. 7A and 7B are top and side views of another barrier having irrigation channels.

FIGS. 10A-10D show a series of steps for trimming the dressing of FIGS. 9A-9B.

FIGS. 16A-16C are views of features of a barrier.

DETAILED DESCRIPTION

The technology disclosed herein generally relates to a system, device and method for negative pressure wound therapy (NPWT). A dressing for NPWT can include a foam sponge pad or wound filler that is placed in the wound and a sealing membrane that covers the wound and the foam sponge pad. A hose can connect the dressing to a vacuum source to apply regulated NPWT to the wound to beneficially facilitate healing of the wound. However, current systems can result in undesirable tissue ingrowth into pores of the foam sponge pad within 2 to 3 days. This ingrowth not only limits the potential safe duration of wear, it also leads to increased pain and wound tissue trauma when the dressing is changed. A barrier can be positioned under the foam sponge pad or wound filler to separate the foam sponge pad away from the wound and to prevent or restrict tissue ingrowth during NPWT. The barrier can be made of a flexible medical grade polymer material and can have complex geometry that can allow flow of fluid and exudate through the barrier during NPWT yet still prevent or restrict the wound tissue from growing into the foam sponge pad or wound filler. The barrier can be used with existing wound dressings that are designed for use without such a barrier, or can be part of a wound dressing where the barrier is attached to the foam sponge pad or other type of wound filler (i.e.

gauze). In this scenario, during the manufacturing of the sponge or wound filler, a similar barrier construct could be attached to the sponge pad/wound filler in order to substantially prevent ingrowth. The barrier could also replace the sponge or wound filler completely. Replacement can be performed at the manufacturing stage by the product manufacturer or at the application stage by the clinician.

Tissue ingrowth is undesirable because it has several consequences. When a dressing is removed after tissue ingrowth into the dressing has occurred, this can result in the tearing of healthy tissue away from the wound surface. This is particularly problematic when the wound exposes critical or delicate structures, such as blood vessels, nerves or visceral organs. This phenomenon results in significant pain with dressing changes and traumatizes the wound tissues, which can be adverse to the healing process. For this reason, dressing changes are required frequently to prevent too much ingrowth, usually within 2 or 3 days, therefore a barrier that prevents or reduces in-growth could allow for extended duration of wear which is a unique clinical benefit of some aspects of this invention. Tissue ingrowth can also result in tearing of the sponge or wound filler resulting in foreign matter being left behind in the wound. These areas of foreign matter can create inflammatory responses, heterotopic ossification and/or infections.

Figure 1:
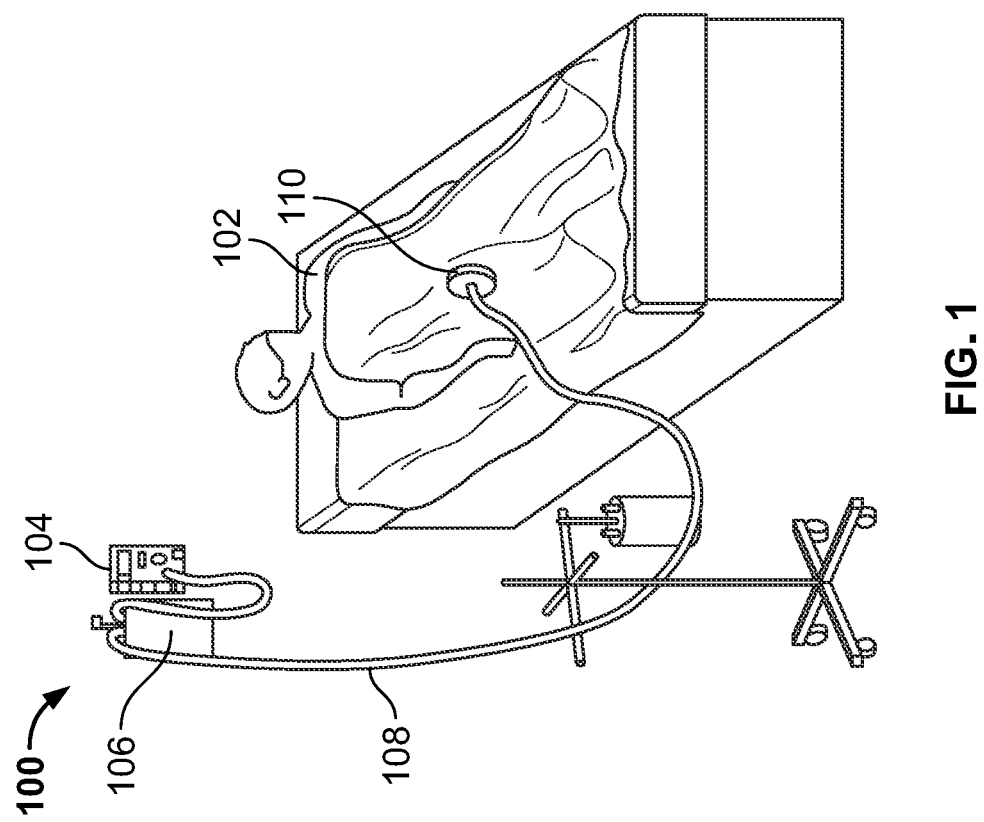
FIG. 1 is a schematic view of a negative pressure wound therapy system (NPWT) and a patient.

FIG. 1 shows a schematic view of a negative pressure wound therapy (NPWT) system 100 and a patient 102 having a wound (not shown in FIG. 1). The NPWT system 100 includes an electronic vacuum regulator (EVR) 104, a canister 106, a tubing system 108, and a wound dressing 110. NPWT can occur in a hospital setting or outside of the hospital with chronic wounds.

The EVR 104 can include a controller (including one or more processors and memory) and a flow rate meter having one or more valves and sensors to measure and control the flow rate of liquid through the EVR 104 and/or the amount of negative pressure applied. In some embodiments, the EVR 104 can include a pump or other device configured to produce negative pressure. In some embodiments, the EVR 104 can be connected to a pump or other device configured to produce negative pressure, such as a wall vacuum source or a dedicated vacuum source.

The wound dressing 110 can be configured to cover and substantially seal a wound of the patient 102. The tubing system 108 can include one or more hoses to connect the wound dressing 110, the canister 106, and the EVR 104 to apply negative pressure (a vacuum) to the wound of the patient 102. The canister 106 can collect liquid removed from the wound of the patient 102.

In some embodiments, the NWPT system 100 can be configured differently than as illustrated. For example, one or more of the EVR 104, the canister 106, the tubing system 108, and the wound dressing 110 can be shaped and positioned differently than as illustrated. Additionally, one or more components can be added, replaced, or removed from the NWPT system 100. For example, the canister 106 can be replaced with a collection bag.

Figure 2:
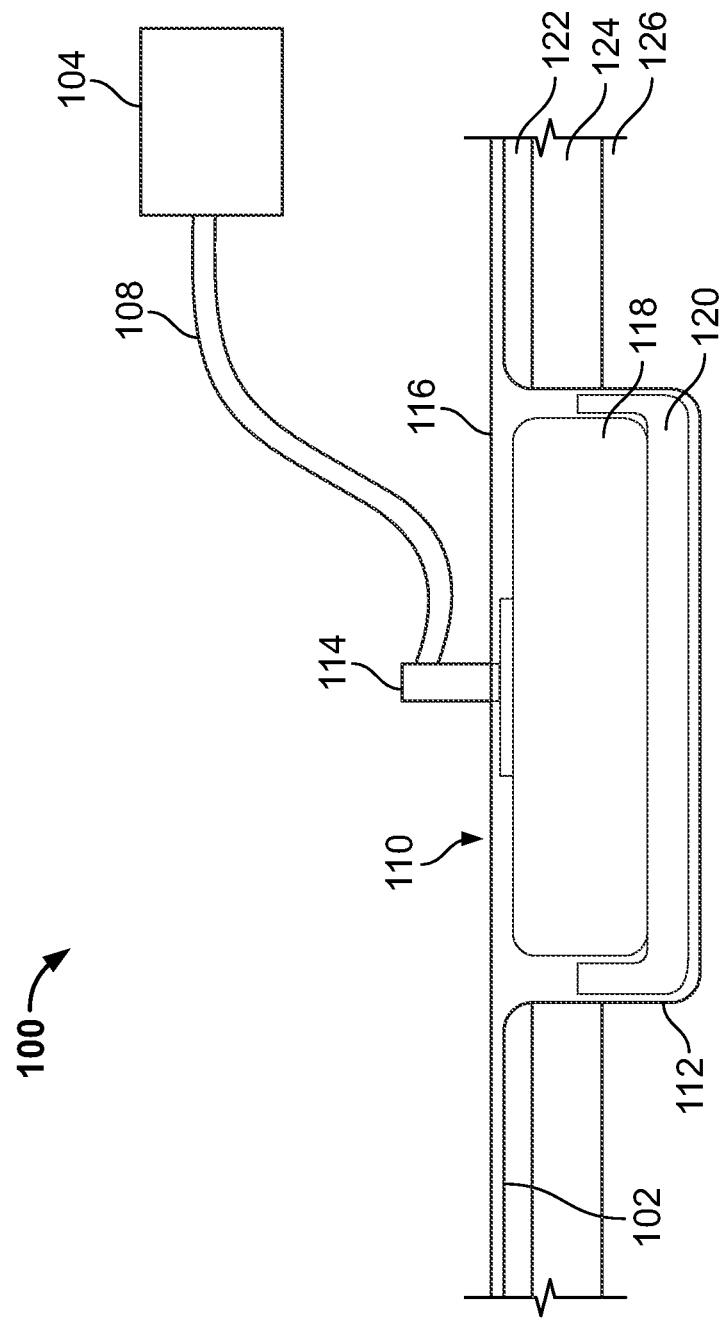
FIG. 2 is a schematic view of a negative pressure wound therapy system.

FIG. 2 is a schematic view of the NWPT system 100, including the EVR 104, the tubing system 108, and the wound dressing 110 (the canister 106 is omitted from FIG. 2).

A portion of the patient 102 is shown including a wound 112. In the illustrated example, the wound 112 is a relatively deep wound into the flesh of the patient 102. The wound 112 can be deep enough to extend through skin tissue 122, through fat tissue 124, and into muscle tissue or visceral spaces 126 of the patient 102. In other examples, the wound 112 can be deeper or less deep depending on the injury to the patient 102.

In the illustrated embodiment, the wound dressing 110 includes a tubing connector 114, a membrane 116, and a pad 118, such as a foam sponge pad, a gauze pad, or other type of wound filler. The pad 118 can be an open cell foam pad (commonly called a sponge) that is cut to size and placed in the wound 112. The membrane 116 can be a relatively thin membrane configured to substantially seal the wound 112. The tubing connector 114 can connect to the tubing system and extend through the membrane 116 to allow for the EVR 104 to apply negative pressure to the wound 112. The pad 118 can be porous to allow flow of liquid and gas between the tubing connector 114 and a surface of the wound 112. The membrane 116 can have an adhesive positioned around a perimeter of the membrane 116 that is configured to stick the membrane 116 to the patient 102 and seal the wound 112 well enough that the EVR 104 can suitably apply negative pressure to the wound 112 to promote new tissue growth.

In some embodiments, an additional barrier 120 can be added under the pad 118. The barrier 120 can be a separation layer that is positioned between the pad 118 and the surface of the wound 112 to space the pad 118 from the surface of the wound 112 and prevent or reduce tissue in-growth into pores of the pad 118.

In some embodiments, the tubing connector 114, the membrane 116, and the pad 118 can be part of a wound dressing 110 for a negative pressure wound therapy system that is intended to be delivered without the barrier 120 and is configured for use without the barrier 120. In such situations, the wound dressing 110 can be intended to be used with the pad 118 placed into the wound 112 and covered by the membrane 116 without placing the barrier 120 under the pad 118. In such situations, NPWT can be performed without the barrier 120, however, doing so can allow for tissue ingrowth into pores of the pad 118. Therefore, the barrier 120 can be provided separately as an additional structure to improve upon an existing wound dressing 110 where the pad 118 is a porous foam material that is susceptible to tissue ingrowth.

The barrier can also be placed to provide protection from desiccation or drying out of susceptible structures such as tendons, nerves, blood vessels, and/or bone. The barrier can be coated with a lubricant such as Vaseline or even antimicrobials such as antibiotics, silver compounds or other materials such as growth factors or other chemicals or medications to promote tissue healing and/or prevent infection.

The barrier 120 can be added as an additional structure in order to prevent or reduce in-growth of tissue (e.g. the muscle tissue or visceral organs 126) into pores of the pad 118. The barrier 120 can space the pad 118 from one or more tissues in order prevent or reduce contact with those tissues. In the illustrated embodiment, the barrier 120 is positioned under the pad 118 and also wrapped at least partially around sides of the pad 118 to space the pad 118 from tissue. In the illustrated embodiment, the barrier 120 is positioned between the pad 118 and the muscle tissue 126, but not necessarily between the pad 118 and the fat tissue 124 (the barrier 120 is shown adjacent to only part of the fat tissue 124) or the skin tissue 122. Such a configuration can be used where it is desired to prevent ingrowth from the muscle tissue 126 while ingrowth by the fat tissue 124 and the skin tissue 122 is deemed to be less of a concern. In other embodiments, the barrier 120 can be larger or smaller and placed to cover more (e.g. covering all or part of each of the skin tissue 122, the fat tissue 124, and/or the muscle tissue 126) or fewer tissues as suitable for the application.

In other embodiments, not illustrated herein, the barrier 120 can be wrapped fully or partially around the pad 118, thereby fully or partially enclosing the pad 118. This particular embodiment would be most useful for deep tracts or tunnels in the wound, in which wound filler is often placed to apply NPWT and prevent loculation. These specific embodiments can have preferred shapes (i.e. cylindrical or rectangular) and dimensions for commonly treated deep wound tracts or tunnels. The advantage of these embodiments over traditional methods, is that the barrier can serve its innovative function of physically separating the wound filler from the wound tissue to prevent or reduce ingrowth in a more circumferential fashion in parts of the wound that have more than just a single planar surface that needs to heal.

As explained above, the barrier 120 can be a structure that is entirely separate from the pad 118, and it can be sold and provided separately for use with a version of the wound dressing 110 that was intended to be used without the barrier 120. In alternative embodiments, the barrier 120 can be attached to the pad 118 and can be sold and delivered together (see, for example, the dressings 610, 710, and 810 described below with respect to FIGS. 15-18). In further alternative embodiments, the barrier 120 can be provided separately from the pad 118, yet be configured to be attached to the pad 118 such as by using one or more fasteners at the time of application of the dressing.

Figure 3:
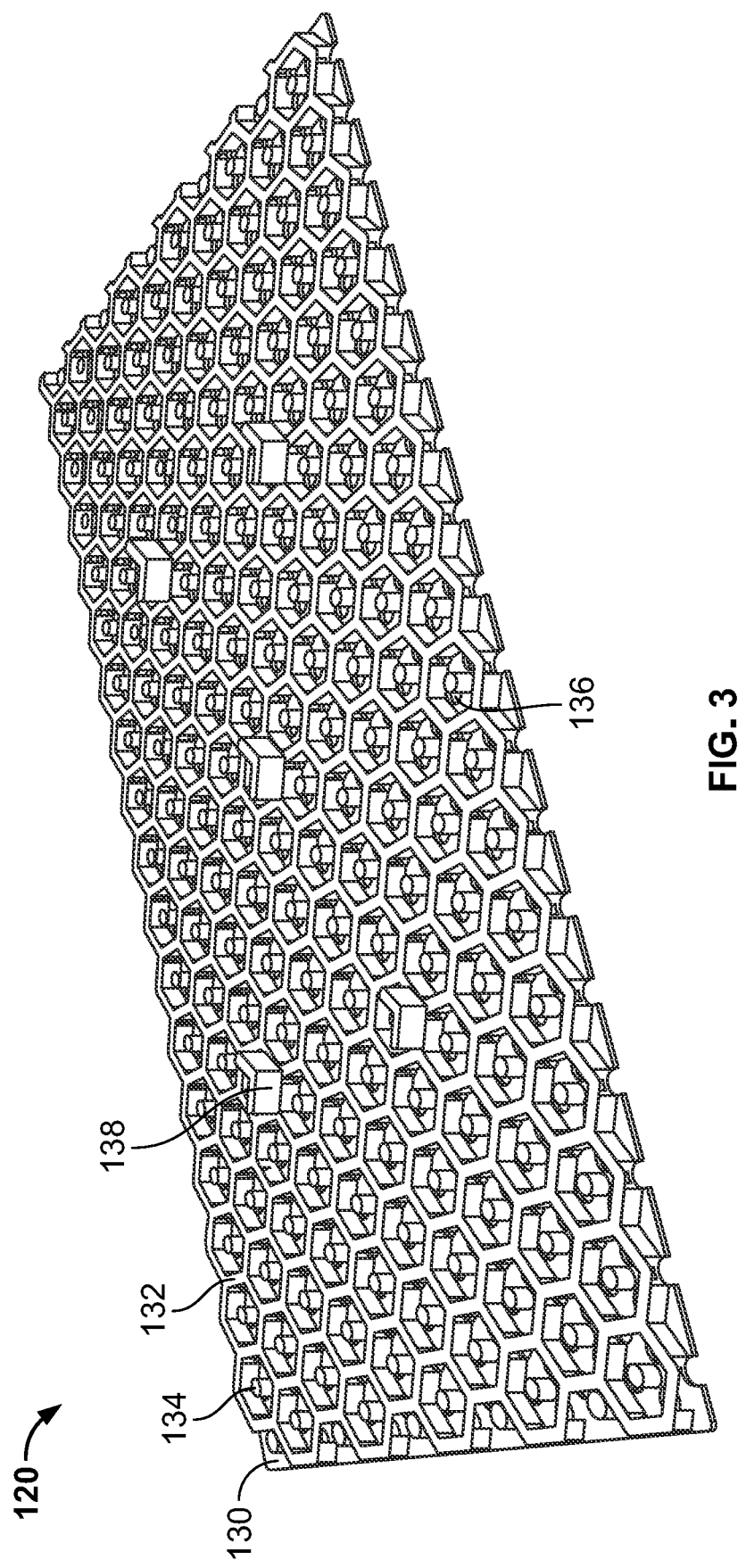
FIG. 3 is a perspective view of a barrier for use in the negative pressure wound therapy system of FIG. 2.
Figure 4:
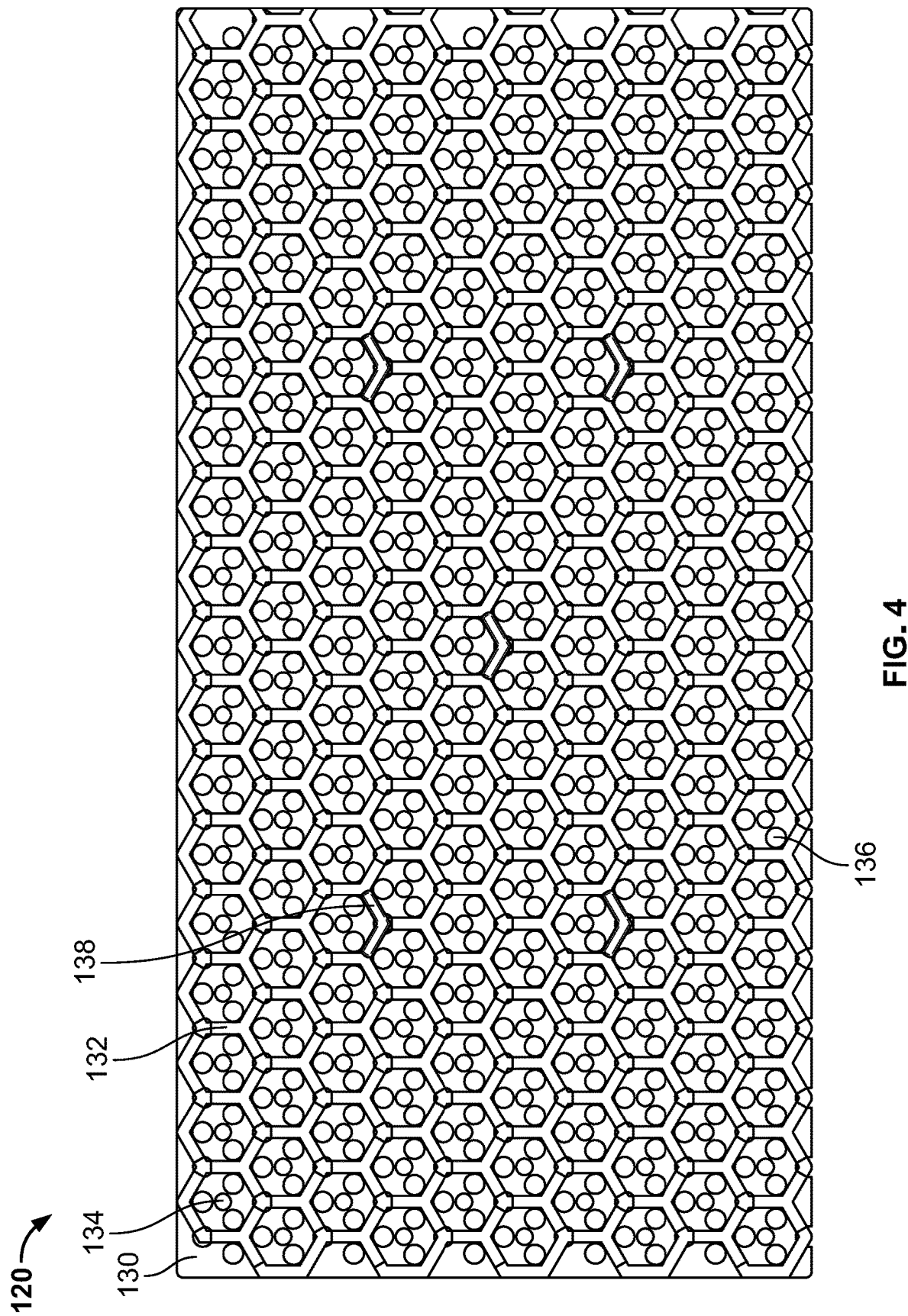
FIG. 4 is a top view of the barrier of FIG. 3.
Figure 5:
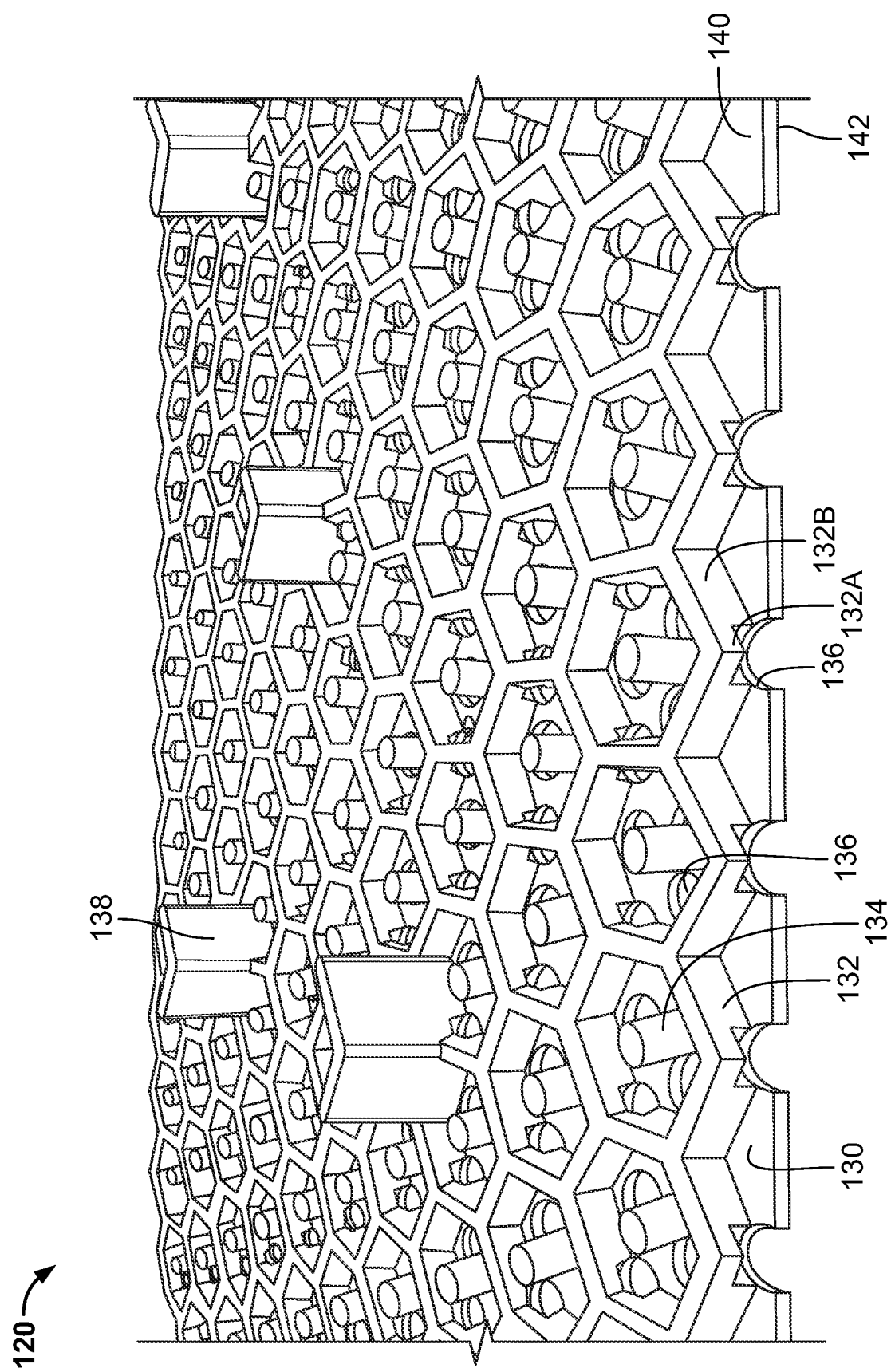
FIG. 5 is an enlarged perspective view of a portion of the barrier of FIG. 3.

The barrier 120 is a porous barrier configured to reduce or prevent tissue ingrowth. In some embodiments, the barrier 120 can be shaped and configured as illustrated in FIGS. 3-5. In other embodiments, the barrier 120 can have different shapes and features as suitable for the application. Multiple layers of different geometric shapes such as circles, hexagons, polygons, screens, etc. can be used to create pathways for suction transmission and fluid or gas passage while still creating a barrier between the solid but compressible sponge or wound filler and the wound. These layers can be separate or manufactured as a single unit. Perforations in the barrier can allow flow both parallel and perpendicular to the surface of the wound to improve or optimize NPWT functionality.

Current sponges or other wound fillers are open cell structures that allow for pieces or parts of the sponge to be left behind in the wound. Likewise, when gauze is used as a wound filler, it can become unraveled also resulting in pieces being left in the wound. The barrier can be created to reduce this by ensuring a closed cell structure. A barrier that is devoid of surface pores that are in the 400-600 micron range for example, can prevent or reduce in-growth into the dressing. Avoiding foreign material being left inside the wound is optimal.

FIG. 3 is a perspective view of the barrier 120. FIG. 4 is a top plan view of the barrier 120. FIG. 5 is an enlarged perspective view of a portion of the barrier 120. The barrier 120 can include complex geometry configured to space tissue away from a porous pad 118 to reduce or prevent tissue ingrowth. Therefore, the barrier 120 provides a physical separation between the wound and the in-growth inducing surface of the wound filler. For example, the barrier 120 can include a base layer 130 and structure extending from the base layer 130, such as walls 132 and posts 134.

The walls 132 can define a repeating polygonal shape, such as the repeating hexagonal shape illustrated in FIG. 3. In other embodiments, the walls 132 can define a different repeating polygonal shape than as illustrated. In other embodiments, the walls 132 can define a different non-polygonal repeating shape, such as repeating circles. In other embodiments, the walls 132 can define different shapes as suitable for the application.

The walls 132 and the posts 134 can extend substantially normally from the base layer 130 to impart thickness to the barrier 120. The posts 134 can be positioned substantially centrally in one, more than one, or all of spaces (or indentations) defined by the walls 132. The posts 134 can provide an offset to help keep tissue (i.e. the muscle tissue 126) or material (i.e. material of the pad 118) out of the spaces defined by the walls 132. In other embodiments, the posts 134 can be omitted if the barrier is shaped and configured to suitably operate without the posts 134.

The base layer 130 of the barrier 120 can define a plurality of perforations (or pores) 136 extending through the base layer 130. The base layer 130 can define one or more perforations 136 extending through the base layer 130 in each of the spaces defined by the walls 132 and can define perforations 136 extending through the base layer 130 at positions under the walls 132. In some embodiments, the perforations 136 are the only passages extending entirely through the base layer 130.

As shown in FIG. 4, the base layer 130 includes three perforations 136 in each of the hexagonal spaces (or indentations) defined between the walls 132. In other embodiments, more or fewer than three perforations 136 can be positioned in each of the spaces defined between the walls 132.

As shown in FIG. 4, the base layer 130 also includes one perforation 136 extending through the base layer 130 at some of the intersections of the walls 132. As shown, the base layer 130 includes perforations 136 under roughly half of the intersections of the walls 132. In other embodiments, the base layer 130 can include more or fewer perforations 136 positioned under the walls 132 than as illustrated.

As best illustrated in FIG. 5, the walls 132 can have a smaller height at portions 132A of the walls 132 that are positioned over perforations 136 and can have a taller height at portions 132B of the walls 132 that are connected to the base layer 130. This can allow for increased flow through perforations 136 that are positioned under the walls 132. This different in wall height also forms passages through the walls 132 that can facilitate flow laterally across the barrier 120.

In some embodiments, the barrier 120 can include one or more tabs 138 extending away from the base layer 130. The tabs 138 can be sized, shaped, and configured to allow for a user (e.g. a doctor or other medical provider) to pull on the tabs 138 to remove the barrier 120 from the wound 112. The tabs 138 can have a strength that is suitable to withstand the force of pulling on the tabs 138 without tearing after the barrier 120 has been left in the wound 112 for an extended period (e.g. several hours or several days). Additional embodiments include suture or wire that can extend outside the barrier 120 to enable or facilitate removal.

In some embodiments, the base layer 130 can be the bottom-most layer of the barrier 120 and be configured for a bottom surface 142 of the base layer 130 to be positioned adjacent the surface of the wound 112. The structure extending up from a top surface 140 of the base layer (e.g. the walls 132 and the posts 134) can be positioned adjacent the porous material of the pad 118. In such embodiments, the barrier 120 can space the pad 118 away from the wound 112 so as to prevent or reduce tissue ingrowth into the pad 118 without additional structure extending from a bottom side of the base layer 130. In some embodiments, the barrier 120 can be manufactured as an integral component of the sponge pad or wound filler 118, such that the two elements are not separate, but one. Such a composite improved NPWT dressing could possess most commonly an open-cell foam sponge superficial surface (i.e. facing away from the wound), whose primary purpose would be to facilitate transmission of negative pressure to the wound and evacuation of wound fluids from the wound 112 surface. Then a barrier layer can be fixedly attached on a wound-facing surface of this composite dressing. Such a barrier layer can serve the same purpose as the barrier 120 does in other embodiments in which the barrier 120 is an independent and separate piece. Such a barrier would be a physical barrier intended to prevent or reduce tissue in-growth into the open-cell foam sponge or other wound filler material. In this way, this embodiment would not be an add on to current NPWT dressings, but rather a uniquely new NPWT dressing with enhanced capability over and above the current art.

In other embodiments, the barrier 120 can have structure extending from both of the top and bottom surfaces 140 and 142 of the base layer 130. For example, the barrier 120 can have walls 132 and posts 134 extending from the bottom surface 142 that are substantially a mirror image to the walls 132 and the posts 134 extending from the top surface 140 (except that the tabs 138 can be omitted). Alternatively, the barrier 120 can have structure extending from the bottom surface 142 of the base layer 130 that is different than the structure extending from the top surface 140 of the base layer 130. Structure that extends from the top surface 140 can be sized, shaped, and configured to interface with the pad 118. Structure that extends from the bottom surface 142 can be sized, shaped, and configured to interface with the muscle tissue 126 or some other tissue of the patient 102 to prevent or resist the muscle tissue 126 from clogging the pores 136 when the muscle tissue 126 grows during the negative pressure wound therapy.

As shown in FIG. 4, the walls 132 can at least partially block at least some of the perforations 136 when viewed from the top (see, e.g., FIG. 4). In some embodiments, the barrier 120 includes structure (e.g. the walls 132) that at least partially block all of the perforations 136 that extend through the base layer 130. In such embodiments, all (or substantially all) of the perforations 136 are at least partially blocked to prevent or reduce tissue growth from extending through the barrier 120 to pores of the pad 118.

The barrier 120 can be a one piece structure with complex geometry. Accordingly, the base layer 130, the walls 132, the posts 134, and the tabs 136 can be integrally formed as a single construct. Alternative designs can allow for the barrier 120 to have multiple layers and allow for removal of some layers to decrease the height of the barrier by the treating provider at the time of dressing application. The barrier 120 can be integrally formed by injection molding via a pliable medical grade polymer. For example, the barrier 120 can be made of silicon or polyurethane. In other embodiments, the barrier 120 can be made of polydioxanone, or another material that is able to dissolve if left implanted in the patient 102 for many days.

The barrier 120 can be constructed of biodegradable material and left in the wound 112 permanently. The barrier 120 can be clear, colored, or tinted to allow for easy identification within the wound 112 in order to prevent it from being left in the wound 112, for versions of the barrier 120 that are not biodegradable. A radiographic marker can be included in the barrier 120 to allow for identification by radiograph, as a means of preventing unintended retention of a dressing in a wound.

In some embodiments, the barrier 120 can be made of a transparent or translucent material. This can allow for better visualization of the wound 112 under the barrier 120. The barrier 120 can also be tinted (such as tinted purple, green, and/or blue) to increase visibility in the wound 112 so as to avoid or reduce the risk of the barrier 120 being undesirably left in the wound 112. In some embodiments, the barrier 120 can be both tinted as well as transparent or translucent. In some embodiments, the tabs 138 (or other removal handles) can be colored and some or all of other portions of the barrier 120 can be clear and not colored.

In some embodiments, the barrier 120 can be formed of a material and can be sized and shaped to be both somewhat pliable and somewhat shape-retaining. For example, the barrier 120 can be pliable enough to bend to conform to a shape of a wound and/or to wrap at least partially around a sponge or other pad 118, such as shown schematically in FIG. 2. Additionally, the barrier 120 can be rigid enough such that the structure (e.g. the walls 132 and posts 134) at least partially retain its shape when placed in the wound 112 under the pad 118 and negative pressure is applied to allow for flow through the barrier 120.

In some embodiments, the barrier 120 can be configured to be cut. Doctors or other medical personnel can cut the barrier 120 to shape so as to fit in the wound 112 depending on the shape of the wound 112. In some of such embodiments, the barrier 120 can also be rigid enough to be held in one hand and cut with the other hand without the barrier 120 sagging undesirably limp during the cutting process.

The barrier 120 can be sized to be relatively long and wide as viewed from the top (see FIG. 4) and to have a relatively thin thickness (or height) as viewed on-edge. For example, the barrier 120 can have a length and width that are each several centimeters long and a thickness that is about 1 to 5 mm thick. In embodiments where the barrier 120 includes the tabs 138, the barrier 120 can have a thickness of 1 to 5 mm not including the tabs 138 such that the tabs 138 effectively increase the thickness of the barrier 120 to more than 1 to 5 mm.

The barrier 120 can have a relatively high tensile strength so as to resist ripping when in tension.

The perforations 136 can be sized large enough to allow for flow through the barrier 120 such that the NPWT system 100 functions effectively to apply negative pressure to the wound 112 below the barrier 120. For example, the perforations 136 can each have a diameter of about 1 to 5 mm. The perforations 136 of the barrier 120 can be sized and shaped to allow for the sucking of liquid and exudate through the perforations 136 without clogging the perforations 136 (or with reduced clogging of the perforations 136).

The walls 132 and/or the posts 134 can have a thickness (when viewed from the top as in FIG. 4) that is small enough to allow the barrier 120 to be flexible and that is large enough to at least partially resist compression when the barrier 120 is placed under the pad 118 and negative pressure is applied. For example, the walls 132 and/or the posts 134 can have a thickness (when viewed from the top as in FIG. 4) of between 1 and 5 mm.

In some embodiments, the barrier 120 can include radiopaque material. Radiopaque material can help ensure that the barrier 120 is visible during x-ray imaging, which, can allow medical professionals to remove the barrier 120 from the patient 102 in the event that the barrier 120 is accidentally left inside the patent after the barrier 120 was supposed to be removed. For example, the barrier 120 can include one or more radiopaque markers such as thin diameter wires (not shown) embedded within flexible, medical-grade polymer material that forms the barrier 120. In some embodiments, a radiopaque thin diameter wire can be positioned in the barrier 120 at the one or more tabs 138 to both reinforce the tabs 138 and to help confirm removal using radiography. The wire or suture can also be used as "rebar" to reinforce the tensile strength of the barrier 120 and resist tearing. The wire or suture in this embodiment would typically be manufactured to lay within the walls of the barrier 120.

In some embodiments, the barrier 120 can include a coating. For example, the barrier 120 can be coated with a lubricant. Coating with a lubricant can be beneficial in situations, such as, when used in wounds with exposed bone or tendon to help prevent (or resist) the bone or tendon from drying out. Alternatively or in addition, the barrier 120 can be coated with a bacteriostatic agent that is configured to stop or slow the reproduction of bacteria. Alternatively or in addition, the barrier 120 can be coated with an antibiotic coating. Moreover, the barrier 120 can be coated with another coating that is deemed suitable for the application.

In some embodiments, the barrier 120 can include irrigation flow channels (e.g. see the irrigation channels of FIGS. 6, 7A, and 7B) extending through the barrier 120. For example, irrigation flow channels can extend through the barrier 120 along a main trunk line flowing through a middle portion of the barrier 120 and with branch lines extending out from the trunk line. Accordingly, such a barrier 120 can allow for irrigation to be supplied to the wound 112 through the flow channels and be suctioned away from the wound 112 through the perforations 136 of the barrier 120 and through the pores of the foam of the pad 118. This type of dressing can support either simultaneous or alternating periods of irrigation and suction. If alternating between suction and irrigation, there can be periods of dwell time between periods spent irrigating or suctioning the wound. If and when trimming of the barrier 120 is desired for the barrier 120 having irrigation flow channels, the barrier 120 could be trimmed in areas where there are branch lines while maintaining the inlet to the trunk line untrimmed. In embodiments that do not require irrigation, the barrier 120 need not include flow channels.

Figure 6:
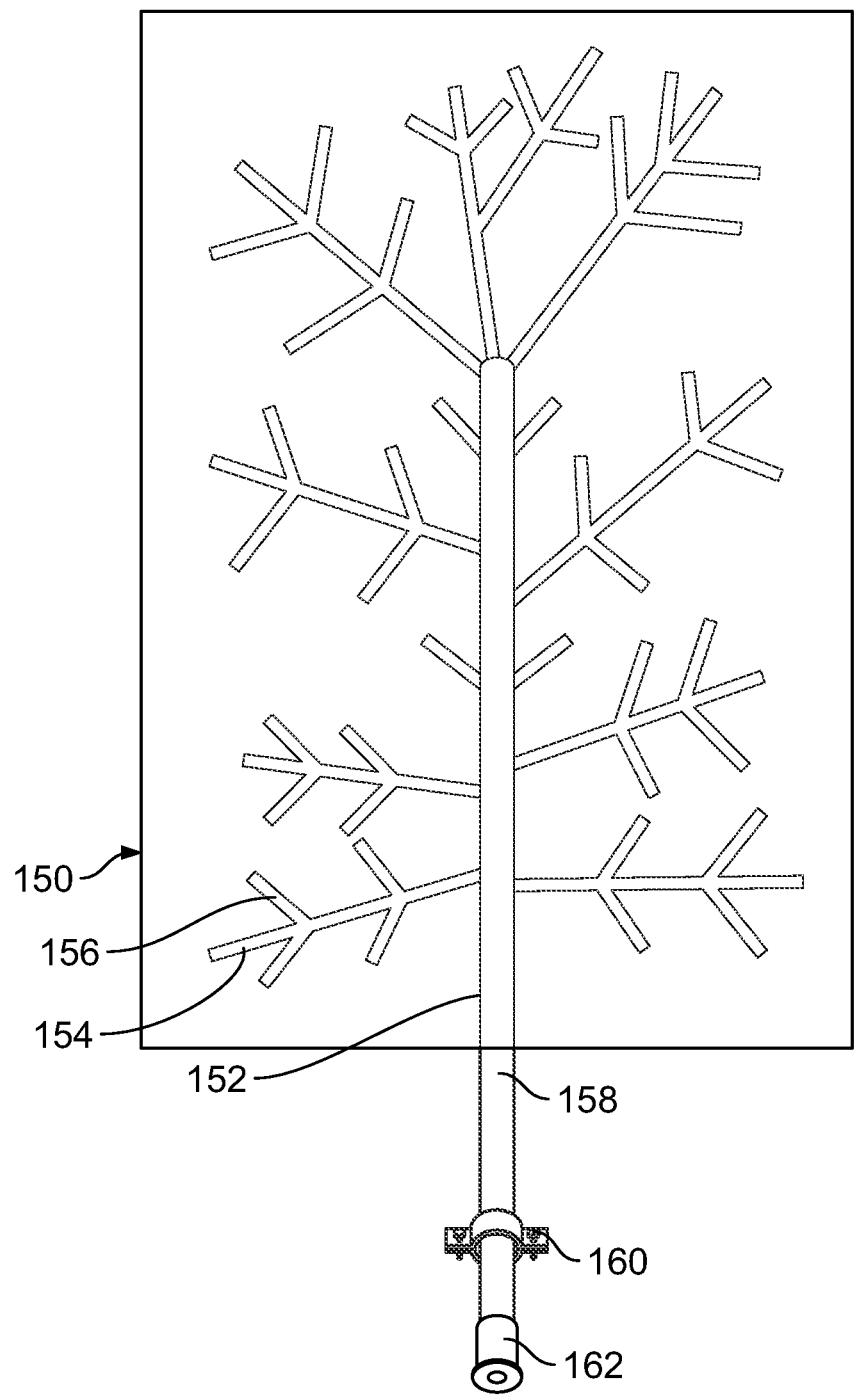
FIG. 6 is a top view of a barrier having irrigation channels.

FIG. 6 is a top view of a barrier 150 having irrigation channels 152, 154, and 156. The irrigation channel 152 can be a main trunk line from which the irrigation channels 154 branch off. The irrigation channels 156 can, in turn, branch off the irrigation channels 154. Accordingly, the irrigation channels 152, 154, and 156 can be oriented similar to the veins in a leaf where a central tube (e.g. the irrigation channel 152) branches into additional tubes (e.g. the irrigation channels 154 and/or 156) to cover the entire surface. This orientation can allow a tube 158 to enter from a side of the barrier 150 to supply irrigant to the barrier 150. In other embodiments, the tube can be positioned substantially normal and central to the non-wound facing surface of the barrier and the irrigation channels can extend radially from this tube. This tube can be long enough to extend through or more than through the common thickness of a wound filler, like foam sponge. In some embodiments, a clamp 160 can be included on the tube 158 to clamp down and seal or restrict flow through the tube 158. In some embodiments, the tube 158 can include a connector 162 for connecting to additional tubing (e.g. to the tubing system 108 described above with respect to FIGS. 1 and 2). In some embodiments, the barrier 150 can be substantially similar to the barrier 120 described above except for the addition of the irrigation channels 152, 154, and 156. In such embodiments, the barrier 150 can be used to supply irrigant to the wound (via the irrigation channels 152, 154, and 156), and simultaneously allow for negative pressure wound therapy, with liquid and exudate sucked through the perforations 136 (not shown in FIG. 6). By allowing for negative pressure wound therapy simultaneously with irrigation, this can reduce or eliminate the need for a dwell time between irrigation and negative pressure wound therapy. In various embodiments, the barrier 150 can have one or more different structures as suitable for the application as a barrier having irrigation channels.

Figure 7A:
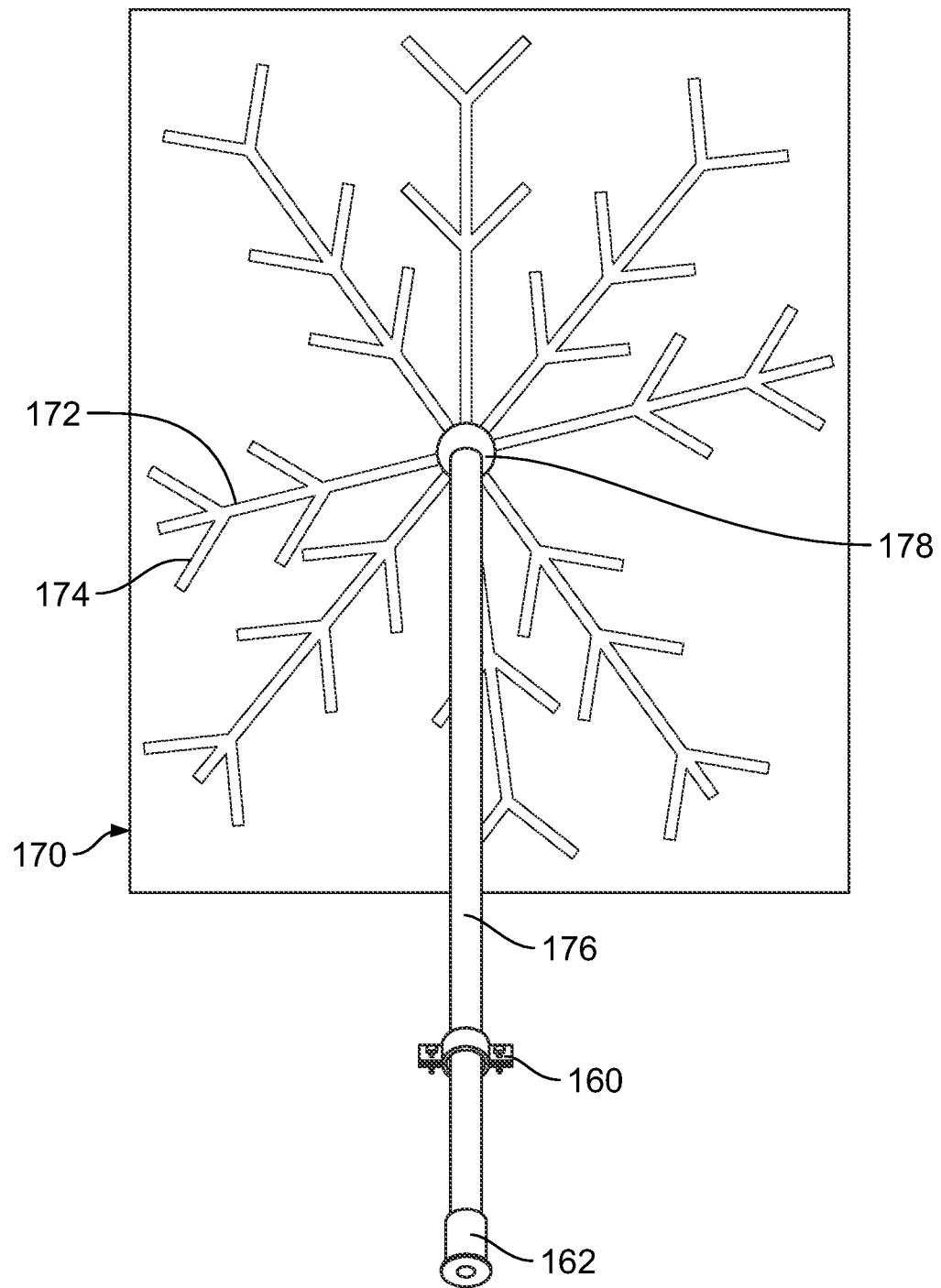
Figure 8:
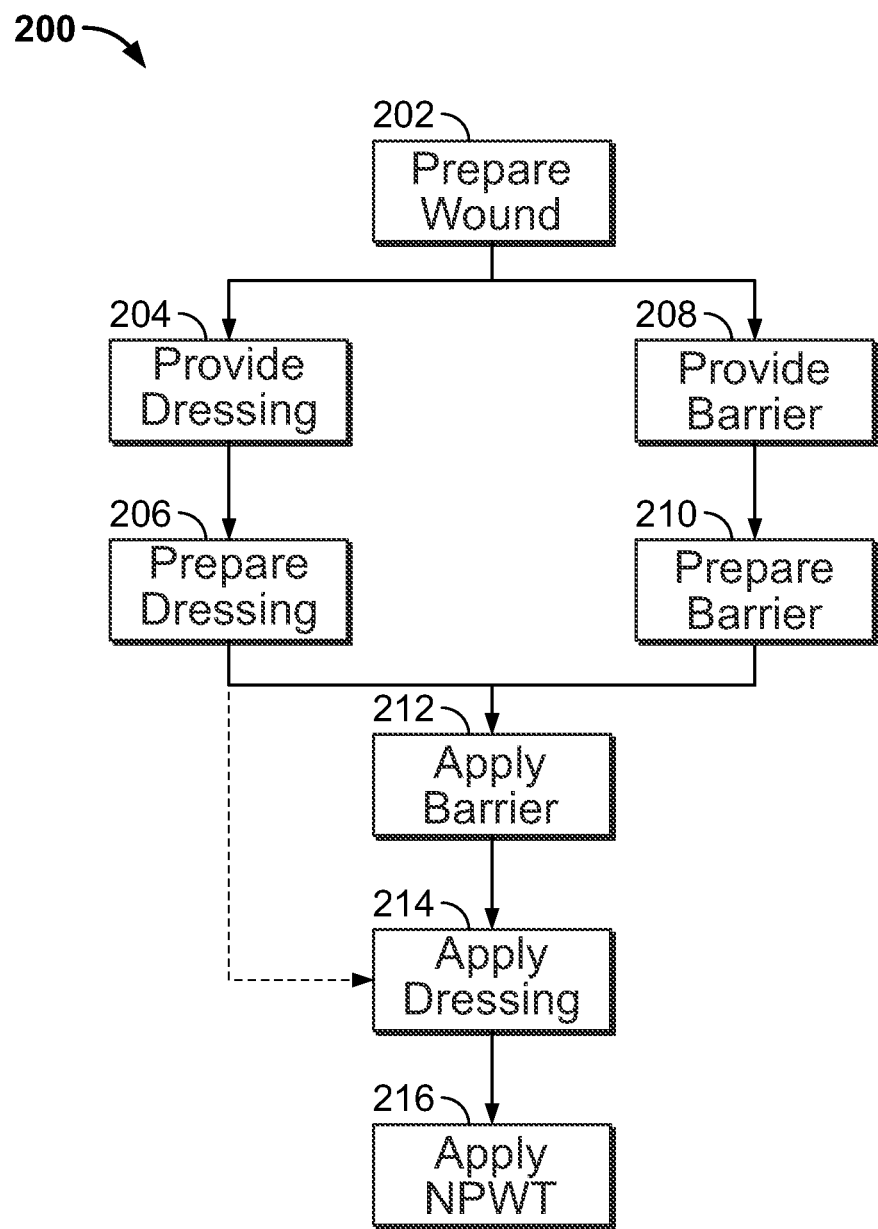
FIG. 8 is a flow chart for a method of using the negative pressure wound therapy system of FIG. 1.

FIGS. 7A and 7B are top and side views of a barrier 170 having irrigation channels 172 and 174. The irrigation channels 172 form multiple main trunk lines from which the irrigation channels 174 branch off. A tube 176 connects to the barrier 170 at a middle portion 178, and the irrigation channels 172 extend radially outward from the middle portion 178. Accordingly, this alternate orientation of the barrier 170 would allow for the tube 176 to be run outside of the barrier 170 (above it) and allow radial tubes (the irrigation channels 172) to be designed to take the irrigation towards a periphery of the barrier 170. The irrigation channels 174 can terminate at outlets 180 that are positioned on a bottom surface of the barrier 170 and/or at the periphery of the barrier 170. Some of the outlets 180 can be positioned proximate a perimeter of the barrier 170 so as to irrigate tissue near the perimeter of the barrier 170 and some of the outlets 180 can be positioned closer to a center of the barrier 170 so as to irrigate tissue near the center of the barrier 170. In alternative embodiments, the barrier 170 can have irrigation channels that are different than those illustrated.

The barriers 150 and 170 can have features (e.g. walls 132, posts 134, and/or perforations 136) and uses that are the same or similar to those described herein for the barrier 120. For example, one of the barriers 150 or 170 can be used in a manner similar to the barrier 120 as described above for FIG. 2, with the barrier 150 or 170 added as an additional structure in order to prevent or reduce in-growth of tissue (e.g. the muscle tissue or visceral organs 126) into pores of the pad 118. The barrier 150 or 170 can be a structure that is entirely separate from the pad 118, and it can be sold and provided separately for use with a version of the wound dressing 110 that was intended to be used without the barrier 150 or 170. In alternative embodiments, the barrier 150 or 170 can be attached to the pad 118 and can be sold and delivered together (see, for example, the dressings 610, 710, and 810 described below with respect to FIGS. 15-18). In further alternative embodiments, the barrier 150 and 170 can be provided separately from the pad 118, yet be configured to be attached to the pad 118 such as by using one or more fasteners at the time of application of the dressing.

In some embodiments, the barriers 150 and 170 can be configured to be trimmed (e.g. via scissors) to substantially match the size of the wound 112 and still function to supply irrigant to the surface of the wound 112. For example for the barrier 150, the tube 158 is attached to the barrier 150 along one edge. Accordingly, the barrier 150 can be trimmed down to size by trimming the other three edges while maintaining the structural integrity of the connection between the tube 158 and the barrier 150. During trimming, one or more of the channels 154 and 156 can be cut and yet the barrier 150 can still function to supply irrigant to the surface of the wound 112 through those portions of the channels 154 and 156 that remain.

Additionally, for the barrier 170, the tube 176 is attached to the barrier 160 at the middle portion 178. Accordingly, the barrier 170 can be trimmed down to size by trimming any of the four edges while maintaining the structural integrity of the connection between the tube 176 and the barrier 170 at the middle portion 178. During trimming, one or more of the channels 172 and 174 can be cut and yet the barrier 170 can still function to supply irrigant to the surface of the wound 112 through those portions of the channels 172 and 174 that remain.

In some embodiments, the barrier 120 (as well as the barriers 150 and 170) can include filaments that act to reinforce the integrity of the barrier 120 in a manner that is similar to rebar in concrete. Such filaments can be in the form of suture material, a metal, a fabric, and/or a stronger polymer. The filaments can be high tensile material that helps resist or prevent portions of the barrier 120 being fragmented and retained in the wound 112.

The filaments can be in a central portion of the barrier 120 in plane with the barrier 120, such that the filaments are in-line to transect or follow the margins of the perforations 136. The filaments can also be in a random pattern to allow for improved tensile strength without being too bulky. In some embodiments, the filaments can be in the form of a mesh layer that is embedded in the barrier 120 prior to the barrier 120 being perforated. A perforating tool can cut a hole in the barrier 120, and also in the mesh filaments imbedded in the barrier 120. Thus, the mesh filaments can optionally be positioned in order to prevent or reduce overlap across the perforations 136.

These filaments can optionally traverse the perforations 136. If the filaments do traverse the perforations 136, the filaments can serve as a sieve to prevent tissue in-growth yet permit the evacuation of wound fluids.

In alternative embodiments, the barrier 120 can be formed as a flat woven mesh layer or a three dimensional mesh structure (such as a pot scrubber or loofah) dipped or coated in silicone or similar material that is bio-compatible/inert. Such a mesh structure could also be similar to a honeycomb type structure. The mesh structure can offer tensile strength and compressibility. The mesh structure can be constructed of suture, metal, polymer, or fabric material. The mesh structure can form a core material that offers tensile strength and that is coated to prevent or reduce tissue ingrowth. Constructing the barrier 120 in this manner can allow for a compressible structure with significant fluid pathways to allow irrigation passage as well as transmit negative pressure. In some embodiments, the barrier 120 can have a structure that is constructed of transparent coating over thin filaments (such as a PDS, proline, monocryl, or woven polyester such as ethibond, fiberwire, or vycryl). The barrier 120 can be made of non-dissolvable or dissolvable material. In another embodiment, the barrier 120 can include a dissolvable polyglycolate material. In another embodiment, the barrier 120 can include collagen based materials to create structural support but still allow a fully dissolvable barrier 120.

In some embodiments, the barrier 120 can also be used with any suitable system as a sponge, pad, or wound filler replacement. By removing the pad 118 (or any other wound filler) and using the barrier 120, the clinician can see the wound 112 assuming the barrier 120 is constructed of a clear material. The tabs 138 can be trimmed to allow for easier sealing over the barrier 120. The barrier 120 can be used with any suitable system that incorporates a sealing layer 102 and suction tubing 108.

FIG. 6 is an example method 200 of using the NPWT system 100. At step 202, the wound 112 of the patient 102 is prepared. This can include cleaning the wound 112, removing necrotic tissue, and/or other procedures deemed necessary or desirable. At step 204, the wound dressing 110 is provided. The wound dressing 110 can include the tubing connector 114, the membrane 116, and the pad 118 (such as a sponge or other filling material). The wound dressing 110 can be intended to be used, and can be suitable to be used, without an additional barrier (such as the barrier 120). However, adding the wound dressing 110 can be beneficially added as described below in steps 208 and 210.

At step 206, the wound dressing 110 is prepared. Components of the wound dressing 110 can be removed from packaging, assembled, and/or trimmed. For example, the pad 118 can be trimmed to a size and shape suitable for being positioned in the wound 112 of the patient 102. The wound dressing 110 can now ready to be applied to the wound 112, except when it is deemed desirable to use the barrier 120. If the wound dressing 110 is to be used without the dressing 112, the method 200 can proceed to step 214. If the benefits of the barrier 120 are desired, steps 208, 210, and 212 can be performed.

At step 208, the barrier 120 is provided. The barrier 120 can be intended for use with the wound dressing 110 and similar wound dressings to improve treatment of the patient 102, yet the barrier 120 is provided separately from the wound dressing 110. At step 210, the barrier 120 is prepared. The barrier 120 can be removed from packaging. In embodiments where the barrier 120 is a single, integrally formed barrier, no assembly is needed. The barrier can be trimmed to a size and shape suitable for being positioned in the wound 112 under the pad 118 to separate the pores of the pad 118 from some or all of the surface of the wound 112.

At step 212, the barrier 120 can be positioned in the wound. The barrier 120 can be positioned to substantially cover all (or substantially all) of the surface of wound tissue. Alternatively, the barrier 120 can be positioned to cover only a portion of the tissue in the wound, such as the muscle tissue 126. Covering the muscle tissue 126 can be beneficial because the muscle tissue 126 can tend to grow into the pores of spongey material like the pad 118, and consequently, pain and tissue damage can result when the pad 118 is removed from the wound 112 when such tissue ingrowth occurs. Other tissue, such as fatty tissue 124, can be less prone to ingrowth, and consequently, it can be less important to cover such fatty tissue 124 in such circumstances. Nonetheless, the fatty tissue 124 and other tissue can also be covered by the barrier 120.

At step 214, the wound dressing 110 can be applied. The pad 118 can be placed in the wound 112 on top of the barrier 120 and the membrane 116 can be applied to cover the wound 112. The tubing connector 114 can be applied so as to connect to tubing for applying NPWT.

At step 216, negative pressure wound therapy (NPWT) can be applied to the wound 112. The EVR 104 can work in conjunction with a vacuum source to apply negative pressure to the wound 112 in order to aid in healing.

When the wound dressing 110 is applied without the barrier 120, the wound dressing 110 can be used for a period of 24-72 hours or less. Even when removed within 24-72 hours or less, tissue ingrowth can occur potentially causing pain, tissue damage, and breakage of portions of the spongy material of the pad 118 and remaining in the wound 112 when the pad 118 is pulled out of the wound 112.

When the wound dressing 110 is applied with the barrier 120 positioned under the pad 118, pain, tissue damage, and/or breakage can be reduced. In some applications, the wound dressing 110 and the barrier 120 can be left in for longer than 24-72 hours because the barrier 120 can inhibit tissue ingrowth. Accordingly, use of the barrier 120 can increase the effective life and duration of each wound dressing 110.

Figure 9A:
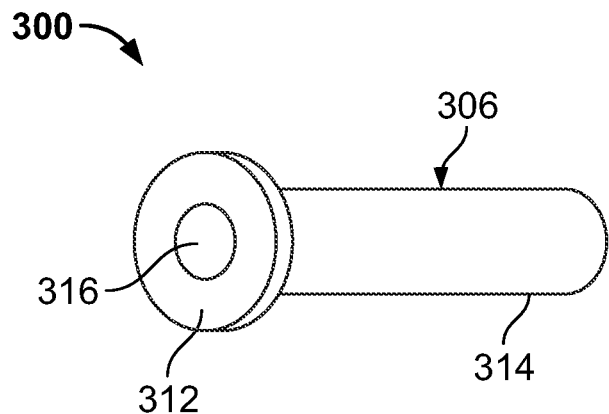
FIG. 9A is a perspective view of a barrier and FIG. 9B perspective views of a dressing using the barrier of FIG. 9A. Both the barrier and the dressing can be configured for use in providing NPWT relatively deep and narrow wounds, such as gunshot wounds and/or cutaneous fistulas.
Figure 9B:
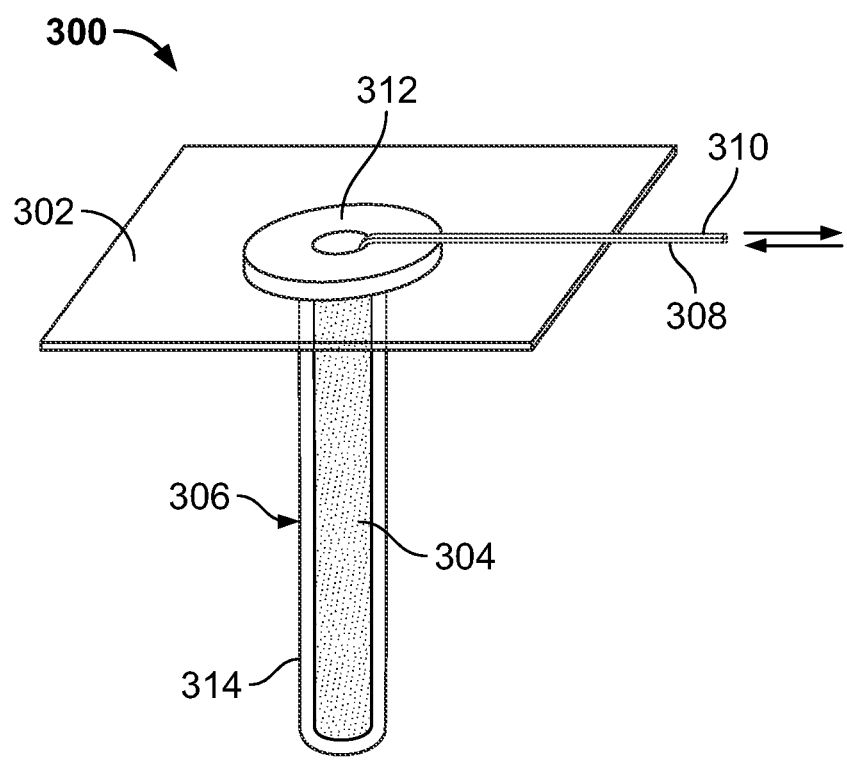

FIGS. 9A-9B show perspective views of a wound dressing 300 for NPWT and a barrier 306 for use in the wound dressing 300. The wound dressing 300 can be suitable for use with relatively long (or deep) and narrow wounds, such as gunshot wounds and/or cutaneous fistulas. The wound dressing 300 can include a membrane 302, a pad 304, and the barrier 306. The barrier 306 can be wrapped substantially or entirely around a circumference of the pad 304. An irrigation tube (or lumen) 308 can be used to supply irrigation to the wound dressing 300. A suction tube (or lumen) 310 can be used to apply negative pressure to the wound dressing 300.

In some embodiments, components and features of the wound dressing 300 can be similar to those described above (e.g. for wound dressing 110) and also have some differences suitable for use in treating relatively long and narrow wounds. For example, the pad 304 can be a foam pad (e.g. a foam sponge) like that described above for the pad 118, except the pad 304 is long and narrow.

Additionally, the barrier 306 can have features similar to barriers described above. For example, some embodiments of the barrier 306 can be a porous barrier (similar to the barrier 120) that provides physical separation between the wound and an in-growth inducing surface of the pad 304. In some embodiments, the barrier 306 can include irrigation channels similar to the barrier 150 or the barrier 170.

As shown in FIG. 9A, the barrier 306 can be substantially nail-shaped, with a relatively broad and flat connection (or head) portion 312 and a relatively long and narrow cylinder (or shaft) portion 314. The barrier 306 defines a relatively long and narrow hollow central core 316. The cylinder portion 314 can be porous to allow fluid flow through the cylinder portion 314 into the central core 316 during NPWT. The cylinder portion 314 can prevent tissue ingrowth into the pad 304 in the central core 316. The barrier 306 can be perforated silicone or other suitable material. The barrier 306 can have a geometric structure, such as a honeycomb shaped structure similar to what is shown in FIG. 3.

FIGS. 10A-10D show a series of steps for trimming the dressing 300. As shown in FIG. 10A, the dressing 300 can be trimmed by cutting through the barrier 306, and possibly the pad 304 as well (e.g. trimming with a knife or scissors). The dressing 300 can be manufactured to a size that is longer than a depth of the wound to be treated, and then be cut to a length that is deemed appropriate for the depth of the wound. As shown in FIG. 10B, the pad 304 can be exposed at a tip of the dressing 300, uncovered by the barrier 306 after being cut. Accordingly, risk of tissue ingrowth can be increased at the tip of the dressing 300 where the pad 304 is uncovered by the barrier 306 due to being cut. As shown in FIG. 10C, a portion of the pad 304 can be pulled out of the distal end of the barrier 306 and then cut shorter. As shown in FIG. 10D, the pad 304 can then be pulled back into the barrier 306 by a distance suitable to prevent or reduce the risk of tissue ingrowth into the pad 304. Accordingly, the dressing 300 can include a gap 318 at the distal end of the dressing 300 where the barrier 306 extends further than the pad 304.

Figure 11A:
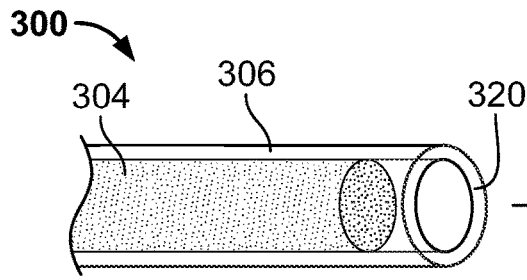
FIGS. 11A-11B show a series of steps for suturing the dressing of FIGS. 9A-9B.
Figure 11B:
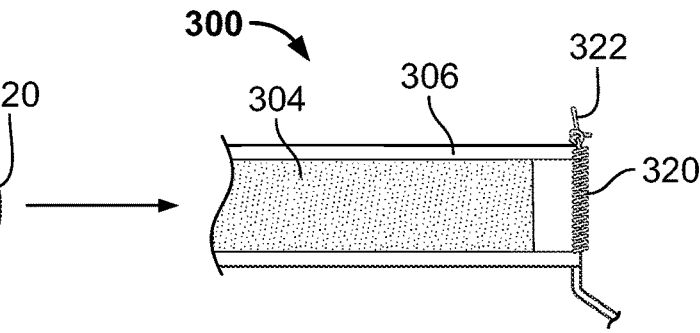

FIGS. 11A-11B show steps for closing the dressing 300 after being cut, such as by suturing. As shown in FIG. 11A, a distal end of the barrier 306 can have an opening 320 after being cut. In some embodiments, the dressing 300 can be sized and shaped such that the barrier 306 can prevent or reduce the risk of tissue ingrowth into the pad 304 even without the opening 320 being closed. In other embodiments, the dressing 300 can benefit from being closed after being cut to size. Accordingly, the opening 320 can be closed, such as by suturing. For example, the opening 320 can be sutured closed via a vessel loop 322. Alternatively the opening 320 can be closed by a silicone bond or other suitable mechanism.

Figure 12:
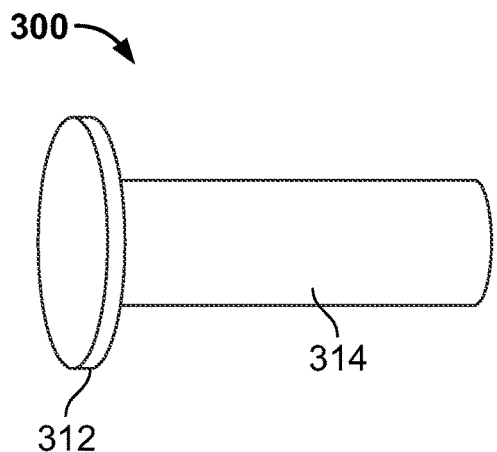
FIG. 12 shows a barrier for a wound dressing having a nail shape.
Figure 13:
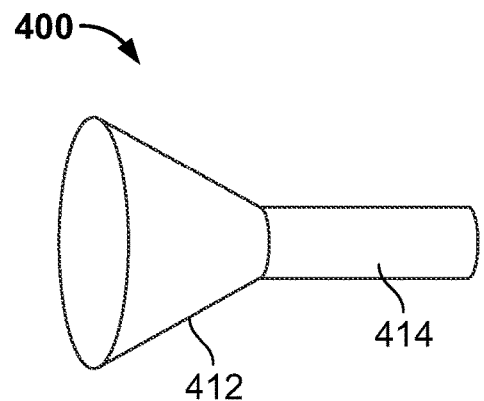
FIG. 13 shows a barrier for a wound dressing having a funnel shape.
Figure 14:
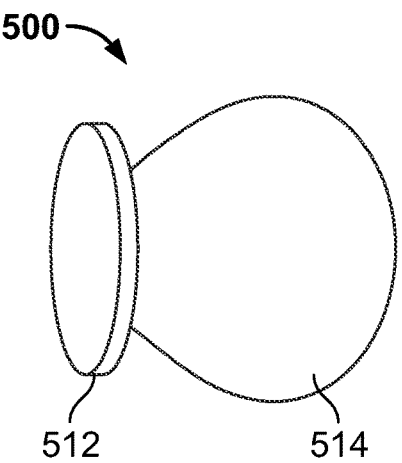
FIG. 14 shows a barrier for a wound dressing having a kettle shape.

FIGS. 12-14 show schematic views of barriers for wound dressings having different shapes. FIG. 12 is a schematic view of the dressing 300 with the barrier 306 that is substantially shaped like a nail. The barrier 306 can have the flat connection (or head) portion 312 and the relatively long and narrow cylinder (or shaft) portion 314. FIG. 13 shows a schematic view of a dressing 400 with a barrier 406 that is substantially shaped like a funnel. The barrier 406 can have a connection portion 412 that is substantially frustoconical and a cylinder portion 414 (similar to the cylinder portion 314) extending from a narrow end of the connection portion 412. FIG. 14 shows a schematic view of a dressing 500 with a barrier 506 that is substantially shaped like a kettle. The barrier 506 can have a connection portion 512 that is relatively wide and flat much like the connection portion 312 of the barrier 306. The barrier 506 can have a shaft portion 514 that is rounded or bulging as compared to the cylinder portion 314 and the cylinder portion 414. Accordingly, FIGS. 12-14 show some of the various shapes suitable for treating relatively deep wounds.

In some embodiments, the barriers 306, 406, and 506 can be used with a pad (e.g. the pad 304 which can be a foam sponge) positioned inside the barriers 306, 406, and 506. In other embodiments, the barriers 306, 406, and 506 can be used without any pad or similar structure positioned inside the barriers 306, 406, and 506.

Figure 15:
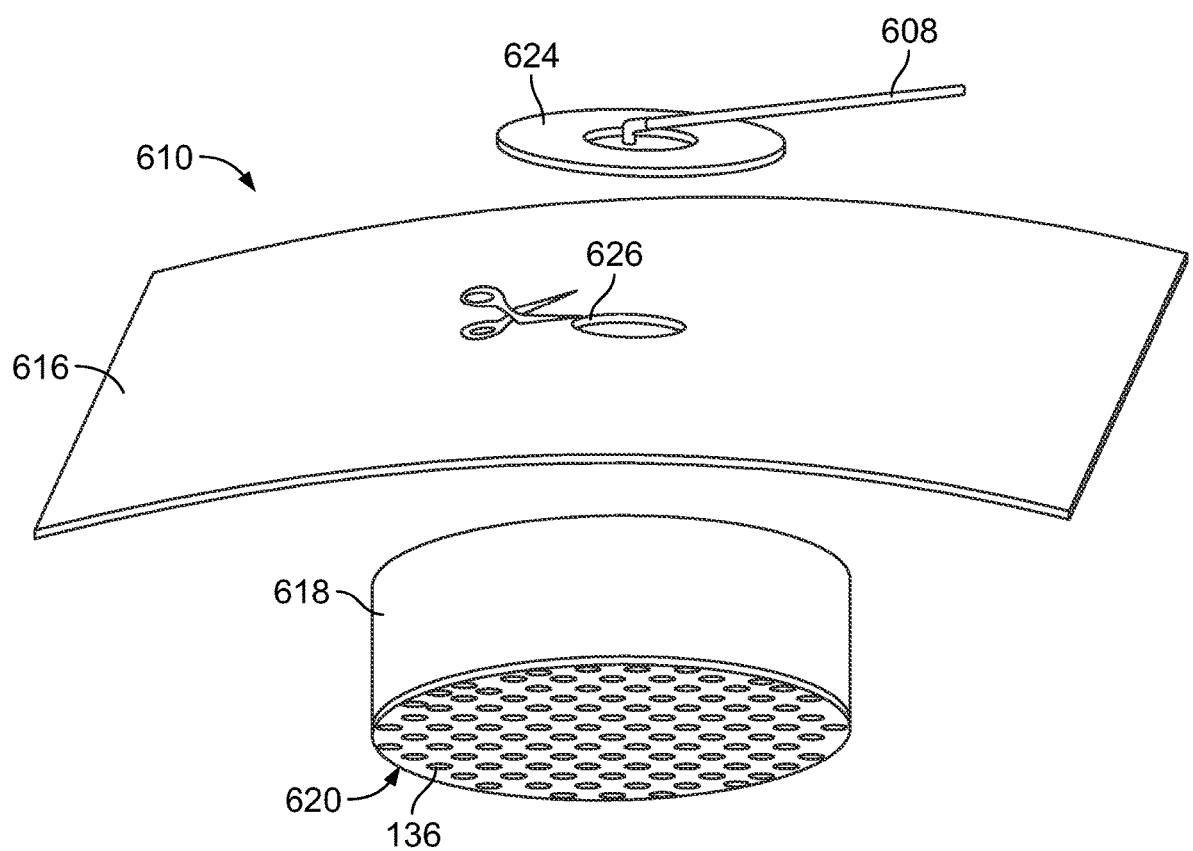
FIG. 15 is a perspective view of a dressing having a combined sponge and barrier.

FIG. 15 is a perspective view of a dressing 610 having a combined pad 618 (such as a sponge) and barrier 620. The barrier 620 can be attached or attachable to the pad 618. In some embodiments, the pad 618 can have a thickness of 1-20 mm and the barrier can have a thickness of 1-4 mm. The barrier 620 and the pad 618 can have some, all, or none of the features described above with respect to other examples of barriers and pads. For example, the barrier 620 can include perforations 136. In some embodiments, the barrier 620 and the pad 618 can be combined and sold together, with the barrier 620 attached to the pad 618. In such embodiments, the user need not assemble the barrier 620 and the pad 618. The barrier 620 and the pad 618 can be sized to fit in a given wound or can be configured to be trimmed together to a size suitable for a given wound (e.g. a user can cut both the barrier 620 and the pad 618 to an appropriate size using scissors while the barrier 620 is attached to the pad 618).

The dressing 610 can include a tubing system 608, a membrane 616, and an adhesive connection layer 624 (e.g. a "lily pad"). The membrane 616 can be positioned over the combined pad 618 and the barrier 620 to cover and seal the pad 618 and the barrier 620 in a wound. A hole 626 can be cut in the membrane 616 at a location aligned with the pad 618 and the adhesive connection layer 624 can be adhered to the membrane 616 at the hole 626 to connect the tubing system 608 to the hole 626 to provide suction to the dressing 610 and the corresponding wound.

FIGS. 16A-16C are views of features of the barrier 620. FIG. 16A shows the barrier 620 having the base layer 130 with a plurality of perforations 136. A plurality of walls 132 can be positioned above (and/or extend from) the base layer 130 to form a honeycomb or other geometric shape. While FIG. 16A shows the barrier 620 having only two honeycomb structures, the barrier 620 can include more honeycomb (or other shaped) structures repeating over some, most, or all of the base layer 130 (see, e.g. FIGS. 3-5). In some embodiments, the barrier 620 can have a combined thickness of the base layer 130 and the walls 132 of 1-5 mm. FIG. 16B shows a view of the base layer 130 and its perforations 136. FIG. 16C shows a view of the walls 132 forming three honeycomb structures.

Figure 17:
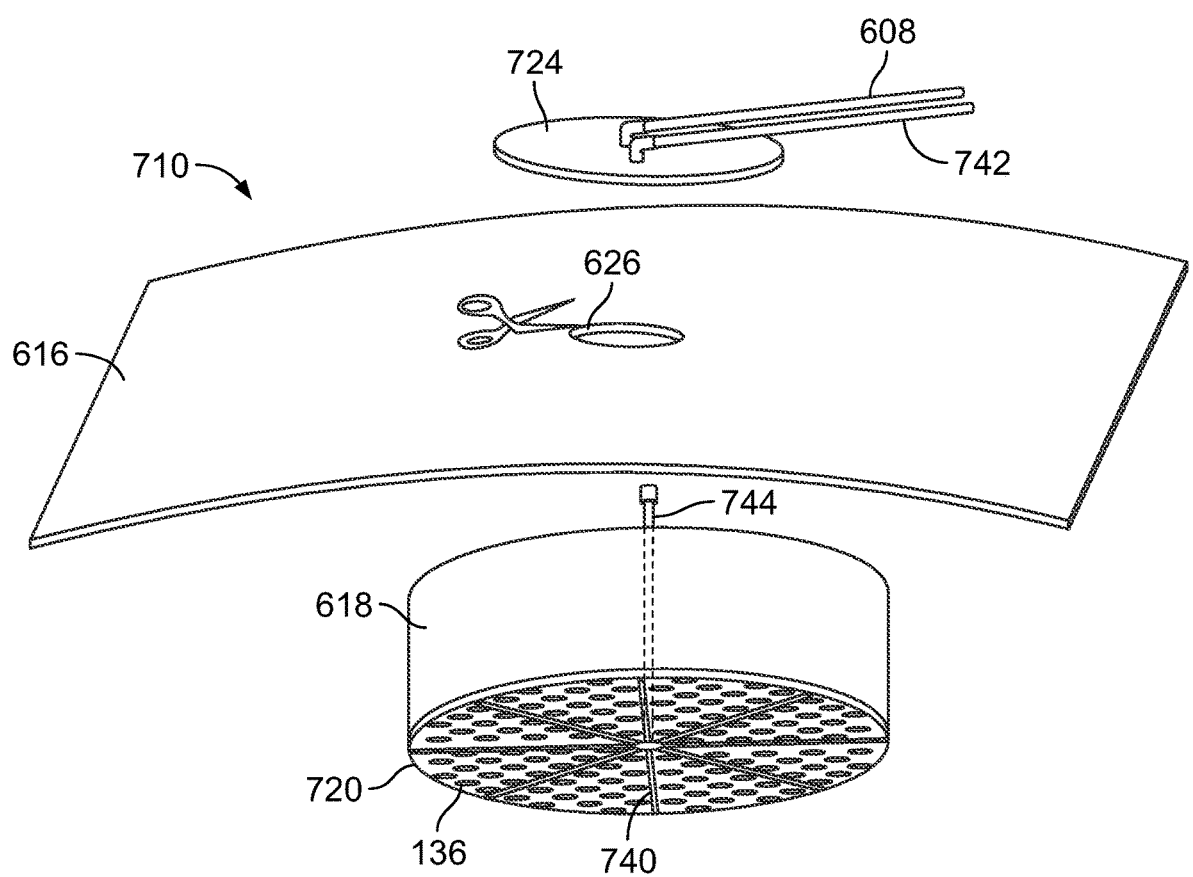
FIG. 17 is a perspective view of a dressing having a combined sponge and barrier with irrigation tubing.

FIG. 17 is a perspective view of a dressing 710 having a combined pad 618 (such as a sponge) and barrier 720 with irrigation tubing 740. The dressing 710 can be similar to the dressing 610 (shown in FIG. 15) except the dressing 710 includes irrigation tubing 740. An irrigation supply tube 742 can be connected to an adhesive connection layer 624 (e.g. a "lily pad") that has connections for both the irrigation supply tube 742 and the tubing system 608 (for providing suction). An extension irrigation tube 744 can extend through the pad 618, connecting the irrigation supply tube 742 to the irrigation tubing 740 in the barrier 720. The irrigation tubing 740 in the barrier 720 can extend radially outward to supply irrigant to a perimeter of the barrier 720. Suction applied via the tubing system 608 can draw irrigant and exudate from the wound up through the perforations 136, through the pad 618, through the adhesive connection layer 724, and out through the tubing system 608.

Figure 18:
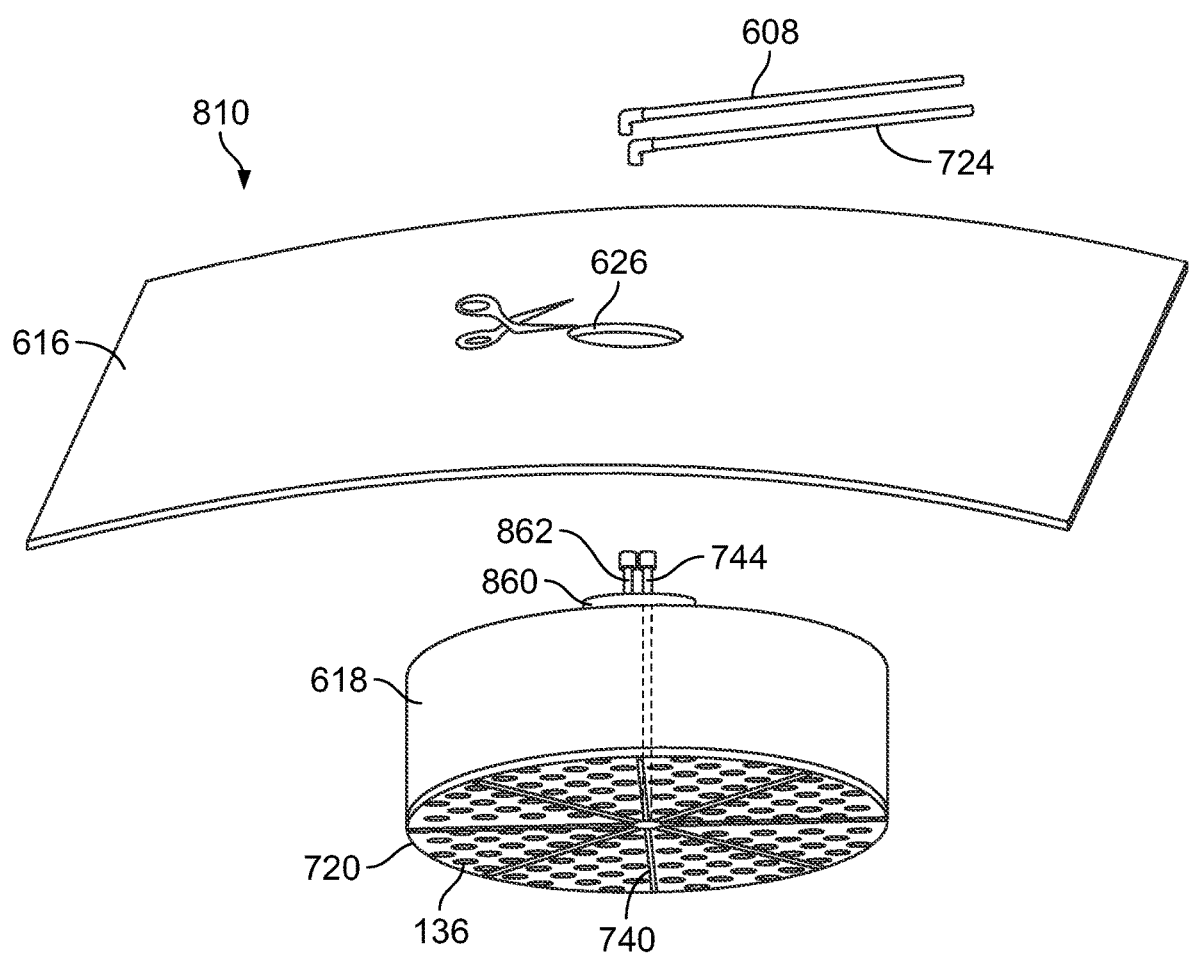
FIG. 18 is a perspective view dressing having a combined sponge and barrier with a suction manifold and irrigation tubing.

FIG. 18 is a perspective view of a dressing 810 having a combined pad 618 (such as a sponge) and barrier 720 with a suction manifold 860 and irrigation tubing 740. The dressing 810 can be similar to the dressing 610 (shown in FIG. 17) except the dressing 810 includes the suction manifold 860. An extension suction tube 862 can connect the suction manifold 860 to the tubing system 608. The suction manifold 860 can be positioned on top of the pad 618 to distribute the suction force over an area on top of the pad 618. Fluid can flow into the suction manifold 860 through a bottom surface of the suction manifold 860 that is either open or substantially open. Fluid can flow out of the suction manifold 860 through a hole in the top of the suction manifold 860 where the extension suction tube 862 is connected to the suction manifold 860.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

A number of embodiments of the inventions have been described. Nevertheless, it will be understood that various modifications can be made without departing from the spirit and scope of the invention. For example, in some embodiments various components such as radiopaque material, filaments, flow passages, etc. need not be included. Moreover, the shape of various features of the barrier can be modified as appropriate. Accordingly, other embodiments are within the scope of the following claims.

What is claimed is:

1. A barrier configured to prevent or reduce in-growth of tissue, the barrier comprising:
    a base layer; and
    walls and posts extending substantially normally from the base layer and imparting thickness to the barrier, wherein the walls define a repeating shape and the posts are positioned substantially centrally in spaces or indentations defined by the walls and providing an offset to help keep tissue out of the spaces or indentations defined by the walls, wherein the base layer defines a plurality of perforations extending therethrough.

2. The barrier of claim 1, wherein the base layer defines one or more of the perforations extending therethrough in each of the spaces or indentations defined by the walls.

3. The barrier of claim 1, wherein the base layer defines one or more of the perforations extending therethrough at positions under the walls.

4. The barrier of claim 1, wherein no passages extend entirely through the base layer except for the perforations.

5. The barrier of claim 1, wherein the walls define a repeating hexagonal shape and the base layer includes three perforations in each of the spaces or indentations defined between the walls.

6. The barrier of claim 1, wherein the base layer includes at least some of the perforations extending through the base layer at some intersections of the walls.

7. The barrier of claim 6, wherein the base layer includes at least some of the perforations under roughly half of the intersections of the walls, wherein the walls have a smaller height at portions of the walls that are positioned over the perforations and a taller height at portions of the walls that are connected to the base layer.

8. The barrier of claim 1, wherein the barrier is made of transparent or translucent material that is configured to allow for visualization of a wound under the barrier when the barrier is in the wound.

9. The barrier of claim 1, wherein the barrier is made of material that is both tinted and transparent.

10. The barrier of claim 1, wherein a first portion of the barrier is transparent and a second portion of the barrier is colored.

11. The barrier of claim 1, wherein the barrier is coated to prevent or reduce tissue ingrowth.

12. The barrier of claim 1, wherein the barrier is sized and shaped to prevent tissue ingrowth.

13. A method of using the barrier of claim 1, the method comprising:
    positioning the barrier in a wound of a patient, wherein the barrier is used without any pad or similar structure;
    covering the barrier while the barrier is in the wound without any pad or similar structure in the wound; and
    applying negative pressure to the wound through the barrier.

14. The method of claim 13, and further comprising:
    visualizing the wound under the barrier by looking through translucent or transparent material of the barrier while the barrier is in the wound; and
    removing the barrier from the wound only after an extended time that is in excess of three days.

15. A system comprising:
    the barrier of claim 1;
    a membrane configured to cover the barrier; and a negative pressure source, wherein the system is configured for use without any pad or similar structure and wherein the system does not include any pad or similar structure.

16. The barrier of claim 1, wherein the barrier is configured to be used without any pad or similar structure.

17. An injection molded polymer barrier that is sized, shaped, and configured to prevent or reduce in-growth of tissue when used in a negative pressure wound therapy system, the injection molded polymer barrier comprising:

a base layer defining a plurality of spaces or indentations passing through the base layer; and structures extending substantially normally from the base layer and imparting thickness to the injection molded polymer barrier, the structures comprising walls surrounding each of the plurality of spaces or indentations passing through the base layer and posts positioned between the walls, wherein the injection molded polymer barrier is integrally formed by injection molding via a pliable medical grade polymer that is transparent or translucent when the injection molded polymer barrier is formed.

18. The injection molded polymer barrier of claim 17, wherein at least the base layer is transparent and wherein at least one or more of the structures extending substantially normally from the base layer is tinted.

19. A barrier comprising:

a transparent or translucent base layer that defines a plurality of perforations extending therethrough; and a plurality of walls and posts extending substantially normally from the transparent or translucent base layer and imparting thickness to the barrier, wherein the walls and posts are configured to provide an offset to reduce or prevent tissue ingrowth, wherein the barrier is integrally formed from a pliable medical grade polymer via injection molding;

wherein the plurality of walls are positioned on the transparent or translucent base layer in a repeating pattern, and wherein the plurality of posts are positioned between the plurality of walls in the repeating pattern.

* * * * *